United States Patent
Martinson et al.

(10) Patent No.: US 9,694,496 B2
(45) Date of Patent: Jul. 4, 2017

(54) PROVIDING PERSONALIZED PATIENT CARE BASED ON ELECTRONIC HEALTH RECORD ASSOCIATED WITH A USER

(71) Applicant: TOYOTA JIDOSHA KABUSHIKI KAISHA, Toyota-shi, Aichi-ken (JP)

(72) Inventors: Eric Martinson, Mountain View, CA (US); Emrah Akin Sisbot, Mountain View, CA (US); Veeraganesh Yalla, Sunnyvale, CA (US); Kentaro Oguchi, Menlo Park, CA (US); Yusuke Nakano, Toyota (JP)

( * ) Notice: Subject to any disclaimer, the term of this patent is extended or adjusted under 35 U.S.C. 154(b) by 85 days.

(21) Appl. No.: 14/632,165

(22) Filed: Feb. 26, 2015

(65) Prior Publication Data

US 2016/0250751 A1 Sep. 1, 2016

(51) Int. Cl.
*G05B 19/04* (2006.01)
*G05B 19/18* (2006.01)
(Continued)

(52) U.S. Cl.
CPC .......... *B25J 9/1674* (2013.01); *B25J 9/163* (2013.01); *B25J 11/009* (2013.01);
(Continued)

(58) Field of Classification Search
CPC ........ B25J 9/163; B25J 9/1674; B25J 11/009; B25J 9/1664; B25J 11/008; B25J 11/0005; B25J 13/08; B25J 13/088; G06F 19/322; G06F 19/3406; G06F 19/3437; G06F 19/345; G06F 3/01; Y10S 901/47; Y10S 901/01; Y10S 901/03; G08B 25/04; G08B 21/04; G06Q 50/22; G06T 7/20
See application file for complete search history.

(56) References Cited

U.S. PATENT DOCUMENTS

2006/0047538 A1* 3/2006 Condurso ............. G06F 19/326
705/3
2008/0001735 A1* 1/2008 Tran .................... G06F 19/3418
340/539.22

(Continued)

FOREIGN PATENT DOCUMENTS

JP 2003-339796 12/2003
JP 2010-140119 6/2010
JP 2013-111737 6/2013

OTHER PUBLICATIONS

Hasimoto "A field study of human support robot in the home environment", Nov. 2013, IEEE.*
(Continued)

*Primary Examiner* — Rachid Bendidi
(74) *Attorney, Agent, or Firm* — Burbage Law, P.C.; Jon-Michael Burbage; Elizabeth Ruzich

(57) ABSTRACT

The disclosure includes methods for determining a current location for a user in an environment; detecting obstacles within the environment; estimating one or more physical capabilities of the user based on an EHR associated with the user; generating, with a processor-based device that is programmed to perform the generating, instructions for a robot to perform a task based on the obstacles within the environment and one or more physical capabilities of the user; and instructing the robot to perform the task.

24 Claims, 9 Drawing Sheets

(51) Int. Cl.
  *B25J 9/16* (2006.01)
  *G06F 19/00* (2011.01)
  *B25J 11/00* (2006.01)

(52) U.S. Cl.
  CPC .......... *G06F 19/322* (2013.01); *G06F 19/345* (2013.01); *G06F 19/3406* (2013.01); *G06F 19/3437* (2013.01); *Y10S 901/01* (2013.01); *Y10S 901/03* (2013.01); *Y10S 901/47* (2013.01)

(56) References Cited

U.S. PATENT DOCUMENTS

| 2011/0288684 | A1* | 11/2011 | Farlow | B25J 11/009 |
| | | | | 700/264 |
| 2012/0072024 | A1* | 3/2012 | Wang | B25J 5/007 |
| | | | | 700/259 |
| 2012/0191464 | A1* | 7/2012 | Stuart | G05D 1/0038 |
| | | | | 705/2 |
| 2013/0245822 | A1* | 9/2013 | Kawanami | B25J 9/1669 |
| | | | | 700/245 |
| 2013/0338525 | A1* | 12/2013 | Allen | A61B 5/1135 |
| | | | | 600/534 |
| 2014/0139616 | A1 | 5/2014 | Pinter et al. | |
| 2014/0279733 | A1* | 9/2014 | Djugash | G06N 99/005 |
| | | | | 706/12 |

OTHER PUBLICATIONS

Sisbot, "A Human-Aware Manipulation Planner", Oct. 2012, IEEE.*
Popescu et al., "An elder care electronic health record system for predictive health assessment," IEEE International Conference on e-Health Networking, Applications and Services, Columbia, MO, 2011, pp. 193-196.
Guillaumin et al., "Multimodal semi-supervised learning for image classification," IEEE conference on computer vision and pattern recognition, San Francisco, CA, 2010, 8 pgs.
Kira et al., "Continuous and Embedded Learning for Multi-Agent Systems," IEEE Proc on the International Conference on Intelligent Robots and Systems, Beijing, China, 2006, pp. 3184-3190.

* cited by examiner

PROVIDING PERSONALIZED PATIENT CARE BASED ON ELECTRONIC HEALTH RECORD ASSOCIATED WITH A USER

BACKGROUND

The specification relates to providing personalized patient care based on an electronic health record associated with a user.

Users with physical limitations often need help managing day-to-day tasks. For example, a user that is confined to a wheelchair may have difficulty picking objects up off the ground or otherwise retrieving objects in their environment. Robots exist that may be able to help a user. For example, a robot may be configured to retrieve objects for users that have difficulty picking objects off the ground.

SUMMARY

According to one innovative aspect of the subject matter described in this disclosure, a method for providing personalized patient care based on an electronic health record associated with a user is described. The method includes determining a current location for a user in an environment; detecting obstacles within the environment; estimating one or more physical capabilities of the user based on an electronic health record (EHR) associated with the user, the EHR including a current medical condition of the user and a historical medical condition of the user; generating instructions for a robot to perform a hand-over motion for moving an object from an original location to a position and rotation in space of a user environment based on the obstacles within the environment and the one or more physical capabilities of the user; instructing the robot to perform the hand-over motion; tracking a status of the user; responsive to a change to the status of the user, generating, with a processor-based device that is programmed to perform the generating, modified instructions for the robot to perform the hand-over motion; and updating the EHR to include the change to the status of the user.

In some implementations, the position and rotation in space of the user environment may include a three dimensional point. The three dimensional point may be a Cartesian (X, Y, Z) point in space included in the user environment that the user will reach or approximately reach when moving their body to receive the object. This three dimensional point may describe the "position" in space where the hand-over event may occur. The user environment includes the area surrounding the user. The three dimensional point may be a surface included in the user environment. For example, the three dimensional point may be configured so that the object is placed on a table surface or some other surface in the user environment. The three dimensional point may be configured so that the object is moved to an empty point in space where the user may reach to receive the object from the robot in accordance with a natural hand-over motion of the user.

The position and rotation in space of the user environment may include a rotation defined by three different dimensions such as roll, pitch and yaw. The roll, pitch and yaw may describe the "rotation" aspect of an actuator of the robot when at or traveling to the hand-over position. The roll, pitch and yaw may change over time as the actuator travels from one point in space to a next point in space. In this way, the rotation of the actuator may be dynamic whereas the position defining the hand-over position is static. In some implementations, the robot may detect events in the environment which cause the hand-over position to change, and so, in this way the handover position may also be dynamic.

The position and rotation in space of the user environment may include other numbers or dimensions to describe that may relate to the posing of the arm joints and/or the trajectory of the arm joints through space.

The one or more physical capabilities of the user may include the conditions or limitations of the user as indicated by the EHR associated with the user. In some implementations, the one or more physical capabilities of the user may include psychological characteristics of the user. For example, if the EHR indicates that a user has a psychological condition, then the instructions for the robot may be modified so that the robot slowly accelerates and decelerates movement in the presence of the user so that the user is not startled or scared by the behavior of the robot (e.g., the robot actuator accelerates at one inch per second squared instead of three inches per second squared).

In general, another innovative aspect of the subject matter described in this disclosure may be embodied in methods that include determining a current location for a user in an environment; detecting obstacles within the environment; estimating one or more physical capabilities of the user based on an EHR associated with the user; generating, with a processor-based device that is programmed to perform the generating, instructions for a robot to perform a task based on the obstacles within the environment and the one or more physical capabilities of the user; and instructing the robot to perform the task.

Other aspects include corresponding methods, systems, apparatus, and computer program products for these and other innovative aspects.

These and other implementations may each optionally include one or more of the following operations and features. For instance, the operations further include: determining a condition of the user based on the EHR and where estimating the path includes estimating a distance between the robot and the user based on the condition of the user; and tracking a status of the user, responsive to a change to the status of the user, generating modified instructions for the robot to perform the task, and updating the EHR to include change to the status of the user. For instance, the features further include: the task being a hand-over motion for moving an object from an original location to a position and rotation in space; estimating the one or more physical capabilities of the user being further based on at least one of a current medical condition of the user and a historical medical condition of the user; estimating the one or more physical capabilities of the user being further based on at least one of a current medical condition of the user and a historical medical condition of the user; the task being a hand-over motion for moving an object from an original location to a position and rotation in space of a user environment and the historical medical condition including at least one of a range of motion for the user, reachability for the user, muscle tension for the user, comfort associated with the user, a preference associated with the user, a time for the user to pick up the object from the robot, a time for the user to make contact with the robot after the hand-over motion, and a time of completion of the task; estimating the one or more physical capabilities of the user being further based on user preferences associated with the user; the task being to carry an object for the user; the task being a hand-over motion and further including determining whether a closest hand that is closest to the robot is injured based on at least one of a range of motion for the closest hand and a reachability for the closest hand and responsive to the closest hand being injured, computing the hand-over motion for moving an object from an original location to a furthest hand that is furthest from the robot; the task being a path for the user to travel, estimating the path for the robot to travel based on at least one of a speed of the user, a relative position to the user, a difficulty of the path, and an amount of information the robot provides to the user for guidance, and further including instructing the robot to guide the user by traveling along the path; where estimating the one or more physical capabilities of the user is based on the EHR and further including building an EHR query, querying a database for the EHR, receiving the EHR, and generating a simulation based on the EHR; and where generating the simulation further includes generating classifiers and training sets that are used to identify a condition associated with the user.

The disclosure is particularly advantageous in a number of respects. For example, a patient's medical history may be used in the construction of new robotic behaviors for interaction. In addition, classifiers for use with specific patents may be improved by incorporating knowledge from an EHR associated with the user. Lastly, tasks can be customized, leading to greater generality of use and less frustration for the user. For example, the robot uses the EHR to reduce the time for searching the environment for an object and retrieving the object. In another example, the robot uses the EHR to provide navigation assistance for the user, based on the EHR, that helps avoid obstacles in the user's environment.

The advantages of the system described herein are provided by way of example, and the system may have numerous other advantages.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

System Overview

Figure 1A:
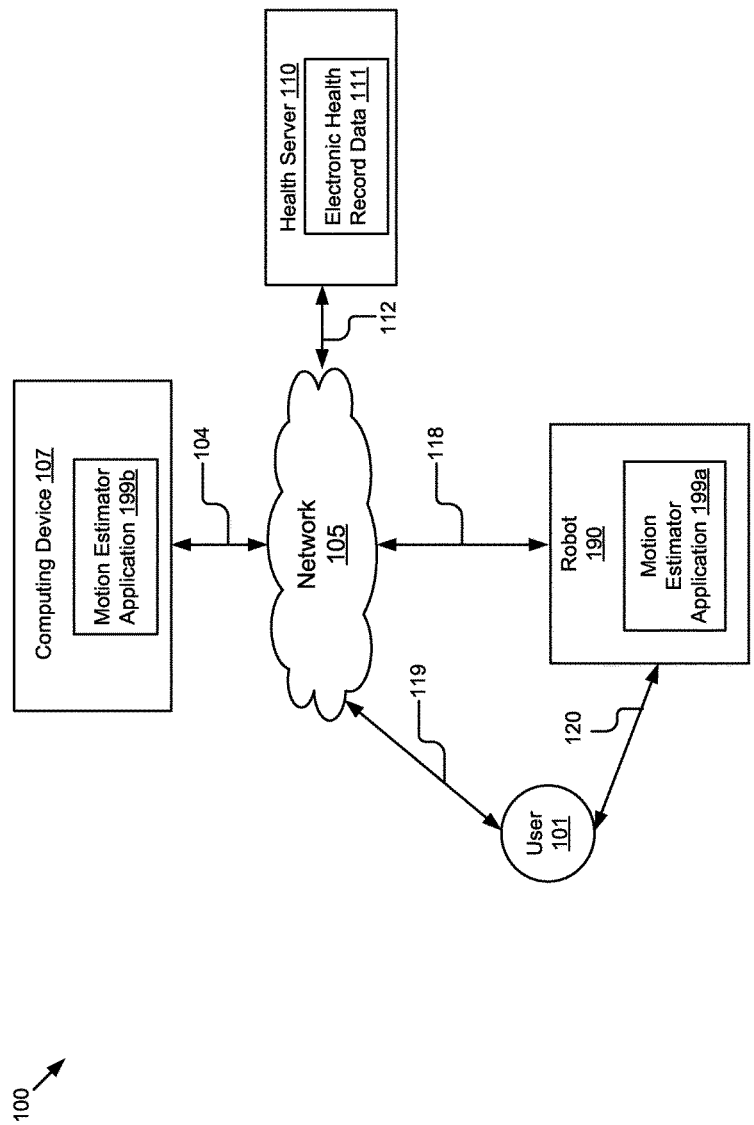
FIG. 1A is a block diagram illustrating an example system for providing personalized patient care based on an electronic health record associated with a user.

A robot may provide services to a user. For example, a robot may perform tasks for a user in a hospital, elder care center, hospice, patient home or other facility. These services may include one or more of the following: monitoring the user; manipulating objects for the user; and guiding the user within an environment.

A problem is created when robots work with users who have physical limitations. The physical limitations may have any cause, including age, illness or temporary or permanent disability. As a result, robot programmers cannot assume that the user is "normal" since the user may suffer from one or more conditions that limit the sight, hearing, standing, walking, grasping ability or other abilities of the user. The robot may harm the user if the robot is not programmed to consider these user conditions and limitations. The robot programmer also cannot assume that all users have conditions or limitations since this may cause the robot to behave in a way that frustrates users and lead to the robots eventual discarding.

Existing solutions have failed to solve the problem of enabling a robot to determine the conditions and limitations of a user and adapt the behavior of the robot accordingly to prevent harm to the user while also not frustrating the user.

For example, some solutions may describe the use of a robot with an electronic health record. However, these solutions do not describe any ability of the robot to identify a user and modify its own program based on the electronic health record associated with the user. Instead, such solutions may describe a robot acting as a proxy for a doctor or other administrator to meet with the patient. The robot may be equipped with technology to enable the doctor to interact with the patient. Accordingly, although such solutions may describe electronic health records, they are inadequate to solve the problem of a robot identifying a user and modifying its own program based on the electronic health record associated with the user so that the robot does not harm the user. By comparison, this disclosure includes a description of a motion estimator application that may beneficially improve the performance of a robot by enabling the robot to identify a user and modify its own program based on the electronic health record associated with the user so that the robot does not harm the user.

Some existing solutions may describing accessing a user's electronic health record and determine activities to perform for the user based on the electronic health record. However, these solutions do not customize the way these activities are performed based on the user's limitations as indicated by the electronic health record so that the user is not injured or scared by the robot. Accordingly, these solutions are unable to solve the problem of enabling a robot to dynamically modify its programming so that the robot behaves in a way that does not harm or scare the patient. By comparison, the motion estimator application described herein may beneficially improve the performance of a robot by enabling a robot to dynamically modify its programming so that the robot behaves in a way that does not harm or scare the patient.

Some solutions may include training visual classifiers. However, training such classifiers is considered to be noisy because this process inherently includes an unacceptably large number of mistakes. Creating a new classifier may include implementation of a large number of images (e.g. between one thousand to one million images) to overcome the noise. As a result, training based on visual classifiers is typically long in duration and not desirable for this reason. By contrast, the motion estimator application described herein may include functionality to improve the quality of a training set for a visual classifier, thereby improving the speed and accuracy of training a visual classifier. Moreover, the motion estimator application may include functionality to create a customized classifier for each user based in part on the electronic health record for the user. The customized classifier may be associated with only one user and configured to enable the robot to customize the programming of the robot for this particular user based on the unique characteristics of this user as indicated by the electronic health record for the user.

Learning new programs may require use of large numbers of examples including both successes and failures. Some solutions may include determining new control behaviors for a robot based on repeated application of a simulation to acquire the large number of examples that may be required for learning new algorithms. However, these solutions do not include customizing the simulation for a particular user based on the electronic health record for the user. By comparison, the motion estimator application may include a customizable simulation that may be tailored to the needs of a particular user, including the specific tasks that may be performed for the user and the way these tasks may be performed for the user based on the user's conditions and limitations as indicated by the user's electronic health record.

The motion estimator application provides numerous other benefits to improve the performance of a robot or computing device. For example, the motion estimator application may customize the control and perception programs of the robot (and thereby modify the behavior of the robot in terms of the robots motion or perception) for one or more users with one or more disabilities. The motion estimator application may access a user's electronic health record and user it to generate one or more positive and negative exemplars from which new robot programs may be trained or existing behaviors may be adapted to provide a customized program for the user (see, for example, element 156 of FIG. 1B).

The motion estimator application may access the electronic health record via a wireless or wired network such as network 105 described below with reference to FIG. 1A. For example, the electronic health record may stored and accessible by a cloud server such as health server 110 described below with reference to FIG. 1A.

In some implementations, the motion estimator application may use the electronic health record to determine a simulation. In this way the simulation may be customized for a particular user and that users disabilities or capabilities as indicated by the electronic health record retrieved by the motion estimator application. The simulation may include, for example, data describing what the user is capable of doing or sensing in their local environment based on their conditions and limitations as indicated by their electronic health record. The simulation may be stored in a tangible memory associated with the motion estimator application such as memory 227 described below with reference to FIG. 2.

The motion estimator application may include a processor and a tangible storage medium. For example, the motion estimator application may be an element of a robot (or alternative a computing device). The simulation provided by the motion estimator application may beneficially improve the performance of the robot. For example, the motion estimator application may include one or more user-specific visual classifiers. The user-specific visual classifier may be associated with a particular user. The motion estimator application may generate a number (e.g., one hundred to one million or more) of positive and negative examples for training the user-specific visual classifier so that the user-specific classifier is tailored for the characteristics of the particular user. An example the positive and negative examples for training the user-specific visual classifier is depicted in FIG. 1C according to some implementations (e.g., training data 170).

The simulation provided by the motion estimator application may beneficially improve the performance of the robot by simulating the effects of different control strategies using one or more of the following techniques: machine learning; system identification; adaptive control; simulation adaptive methods; and simulating how changes to input parameters to the code and routines of the robot affect success rate.

The simulation provided by the motion estimator application may beneficially improve the performance of the robot by simulating the effects of different control strategies using one or more of the following techniques: machine learning; system identification; adaptive control; simulation adaptive methods; and simulating how changes to input parameters to the code and routines of the robot affect success rate.

The simulation provided by the motion estimator application may beneficially improve the performance of the robot by reducing the search space of an object retrieval or person detection task for the robot. For example, assume that the robot has the task of retrieving a user object from an environment proximate to the user. Without the simulation provided by the motion estimator application, the robot may need to search within this environment using environmental sensors (e.g., external camera, etc.) or by probing the environment using an actuator configured for object retrieval. However, the one or more simulations provided by the motion estimator application may include data describing this environment and the objects that may be included in this environment. Accordingly, using the simulation, the robot may reduce the space within the environment that must be analyzed or searched in order to identify the object, navigate to the object and successfully retrieve the object.

As a result of the above described benefits, the motion estimator application beneficially improves the performance of robot programs (and the robot behaviors resulting from execution of these robot programs, whether they be the motion of the robot or the perception of the robot). The one or more simulations provided by the motion estimator application may also be used to customize one or more robot programs based on an electronic health record for a particular user being serviced by the robot. In this way, the motion estimator application may beneficially customize the robot program for the disabilities or capabilities of a particular user. The robot may repeat this process for different users by utilizing different user-specific visual classifiers and the electronic health record for these users, thereby making the robot more useful to a diverse population of additional users having similar or different disabilities or capabilities as the particular user.

FIG. 1A illustrates a block diagram of some implementations of a system 100 for providing personalized patient care based on an electronic health record associated with a user. The system 100 includes a computing device 107 communicatively coupled to a network 105 via a signal line 104, a robot 190 communicatively coupled to the network 105 via a signal line 118, a health server 110 communicatively coupled to the network 105 via signal line 112, and a user 101 communicatively coupled to the network 105 via signal line 119 and communicatively coupled to the robot 190 via signal line 120.

While FIG. 1A illustrates one user 101, one computing device 107, one health server 110, and one robot 190, the disclosure applies to a system architecture including one or more users 101, one or more computing devices 107, one or more health servers 110, and one or more robots 190. Furthermore, although FIG. 1A illustrates one network 105 coupled to the entities of the system 100, in practice one or more networks 105 of various types may be connected to these entities.

The network 105 can include a conventional type, wired or wireless, and may have numerous different configurations including a star configuration, token ring configuration, or other configurations. Furthermore, the network 105 may include a local area network (LAN), a wide area network (WAN) (e.g., the Internet), or other interconnected data paths across which multiple devices may communicate. In some implementations, the network 105 may be a peer-to-peer network. The network 105 may also be coupled to or include portions of a telecommunications network for sending data in a variety of different communication protocols. In some implementations, the network 105 includes Bluetooth® communication networks or a cellular communications network for sending and receiving data including via short messaging service (SMS), multimedia messaging service (MMS), hypertext transfer protocol (HTTP), direct data connection, WAP, e-mail, etc. In some implementations, the network 105 may include a global positioning system (GPS) satellite for providing GPS navigation to the robot 190. The network 105 may be a mobile data network, for example, 3G, 4G, LTE, Voice-over-LTE ("VoLTE"), or any other mobile data network or combination of mobile data networks. In some implementations, the network 105 may be a combination of different networks.

The health server 110 can include a hardware server that includes a processor, a memory, and network communication capabilities. The health server 110 may generate and/or store electronic health record (EHR) data 111. For example, the health server 110 may be part of a centralized system to provide users with EHR data 111, or the health server 110 may be associated with a single healthcare institution (e.g. a hospital, a doctor's office, etc.). The health server 110 may receive a request from the computing device 107 or the robot 190 to transmit an EHR for the user 101. The health server 110 may use HL7 messaging to transmit an encrypted EHR that complies with the Health Insurance Portability and Accountability Act of 1996 (HIPAA).

In some implementations, the motion estimator application 199a may be operable on the robot 190. The robot 190 can include a memory, a processor, and hardware for facilitating mobility of the robot 190. The robot 190 performs a task for the user 101. For example, the robot 190 may perform a hand-over motion for moving an object from an original location to a position and rotation in space of the user environment by picking up the object and moving the object to the position and rotation in space. In another example, the robot 190 guides the user on a path. In yet another example, the robot 190 carries an object for the user 101. The user 101 may interact with the motion estimator application 199a on the robot 190 using voice commands or by interacting with the motion estimator application 199b on the computing device 107, which transmits data to the motion estimator application 199a on the robot 190.

In some implementations, position and rotation in space may include a three dimensional point may be a Cartesian (X, Y, Z) point in space included in the user environment that the user will reach or approximately reach when moving their body to receive the object. The position and rotation in space may also include rotational data describing the rotation. For example, the position and rotation in space may include rotational data describing a roll, pitch and yaw orientation for the robot 190 or an actuator of the robot 190.

In some implementations, the three dimensional point and the rotational data (the roll, pitch and yaw) may be determined based on simulation data describing one or more simulations for the robot. For example, the simulation data may describe a reach simulation that includes data describing the how the user is expected to move their body in order to receive the object from the robot.

The user environment may include the area surrounding the user. The three dimensional point may be a surface included in the user environment. For example, the three dimensional point may be configured so that the object is placed on a table surface or some other surface in the user environment. The three dimensional point may be configured so that the object is moved to an empty point in space where the user may reach to receive the object from the robot in accordance with a natural hand-over motion of the user.

In some implementations, the simulation data may describe other types of simulations. For example, the simulation data may describe how the user will walk or run in order to navigate in the user environment.

In some implementations, the motion estimator application 199b may be operable on the computing device 107. The computing device 107 may be a computing device that includes a memory and a processor, for example, a desktop computer, a laptop computer, a tablet computer, a mobile telephone, a smartphone, a personal digital assistant (PDA), a mobile e-mail device, a wearable device including a smartwatch, a portable game player, a portable music player, or other portable electronic device capable of accessing the network 105. The computing device 107 may be part of a server and accessible to the user 101 via a browser.

The motion estimator application 199a and 199b may be referred to herein individually and collectively as "motion estimator application 199." In some implementations, modules of the motion estimator application 199 can be stored in a single server or device. In some other implementations, modules of the motion estimator application 199 can be distributed and stored across multiple servers or devices. For example, the motion estimator application 199a on the robot 190 may determine a current location for the user 101, transmit the location to the motion estimator application 199b on the computing device 107, and receive instructions from the motion estimator application 199b on the computing device 107 to perform a task. Furthermore, the separation of various components, modules, and servers in the implementations described herein should not be understood as requiring such separation in all implementations. In some implementations, the described components, modules, devices, or servers can generally be integrated together in a single component, module, device, or server.

The motion estimator application 199 may include code and routines for determining a current location for the user 101. For example, the robot 190 may include a camera that captures images of the user 101 to determine a position of the user 101 in relation to the robot 190. The motion estimator application 199 detects obstacles within the environment. For example, the motion estimator application 199 detects the location of objects on a floor and a width between doorways. The motion estimator application 199 estimates the one or more physical capabilities of the user 101 based on an EHR associated with the user 101. For example, the EHR may identify the user 101 as being blind. The EHR may be received from the health server 110 or generated by the motion estimator application 199. The motion estimator application 199 generates instructions for the robot 190 to perform a task based on the obstacles within the environment and the one or more physical capabilities of the user 101. For example, a blind user 101 would be helped by a robot 190 acting as a guide to warn the user of obstacles on the floor and to help the user navigate through the doorway. The motion estimator application 199 instructs the robot 190 to perform the task.

In some implementations, the motion estimator application 199 can be implemented using hardware including a field-programmable gate array ("FPGA") or an application-specific integrated circuit ("ASIC"). In some other implementations, the motion estimator application 199 can be implemented using a combination of hardware and software. The motion estimator application 199 may be stored in a combination of the devices and servers, or in one of the devices or servers.

Figure 1B:
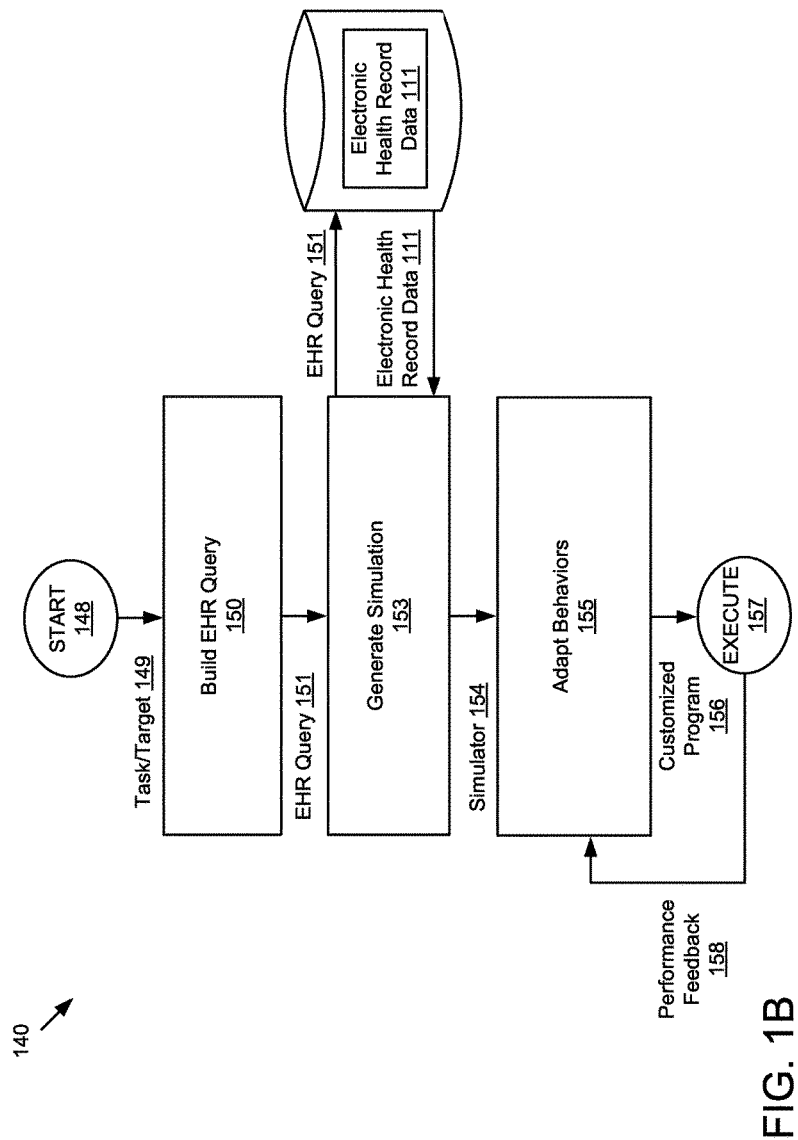
FIG. 1B is a block diagram illustrating an example process flow for providing personalized patient care based on an electronic health record associated with a user.
Figure 1C:
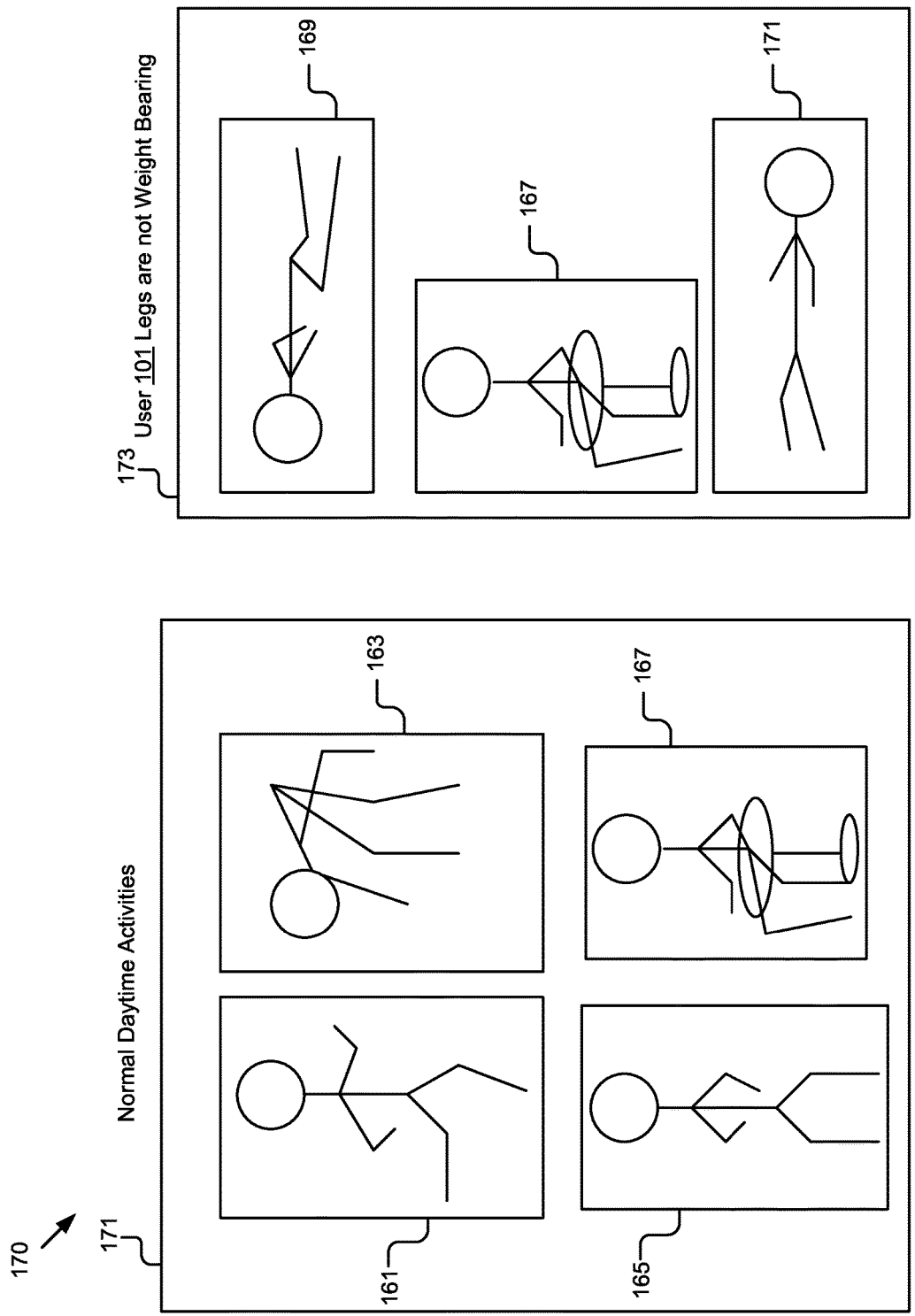
FIG. 1C is a block diagram illustrating example training data for training a user-specific visual classifier.

FIG. 1B is a block diagram illustrating an example process flow 140 for providing personalized patient care based on an electronic health record associated with the user 101. The process flow 140 may be implemented by one or more elements of system 100 described above with reference to FIG. 1A. For example, the process flow 140 may be implemented by the motion estimator application 199 and the health server 110. Elements 148, 150, 153, 155, 157 and 158 may be executed by the motion estimator application 199. The querying process of elements 151 and 152 may be executed in part by the health server 110. In the depicted implementation of FIG. 1B, the electronic record data 111 may be stored in a database hosted by the health server 110. The motion estimator application 199 may include code and routines configured to provide the functionality described below with reference to one or more of elements 148, 150, 153, 155, 157 and 158.

The process flow 140 may include four stages. The process flow may start 148. A task and a target identifier may be provided to the motion estimator application 199. The task may include data describing a task to be performed by the robot 190 or the computing device 107. The target identifier may include data identifying a user 101 or location within an environment associated with the task. The motion estimator application 199 may build 150 the EHR query 151 based on the task and the target identifier. The motion estimator application 199 may use the EHR query 151 to retrieve electronic health record data 111 associated with the user 101. The motion estimator application 199 may generate 153 a simulation 154 based on the electronic health record data 111. The motion estimator application 199 may adapt 155 the behaviors of the robot 190 or computing device 107 based on the simulator 154. In this way, the motion estimator application 199 may determine a customized program 156 for the robot or computing device 107. The customized program 156 is customized based on the electronic health record data 111 for the user 101. The motion estimator application 199 may execute 157 the customized program 156. As an optional feature, the motion estimator application 199 may determine performance feedback 158 based on the execution of the customized program 156. The performance feedback 158 may include data describing the performance, successes or failures of the customized program in providing service to the user 101. The motion estimator application 199 may use the performance feedback to further improve the performance of future customized programs 156. For example, the performance feedback data describing the performance feedback 158 may be added to the electronic health record data 111 associated with the user 101. In this way the motion estimator application 199 may improve the performance of the robot 190 or the computing device 107.

FIG. 1C is a block diagram illustrating example training data 170 for training a user-specific visual classifier. The classifier data 292 described below with reference to FIG. 2 may include, among other things, data describing one or more user-specific visual classifiers. The training data 170 may be stored on a tangible memory such as memory 227 described below with reference to FIG. 2. For example, the training data 170 may be included as an element of the classifier data 292.

The motion estimator application 199 may include code and routines for training one or more user-specific visual classifiers using the training data 170. The motion estimator application 199 may build new user-specific visual classifiers or update existing user-specific visual classifiers using the training data 170. The user-specific visual classifier may be built or updated offline, prior to a robot 190 encountering the particular user 101 or responsive to one or more current or future tasks to be performed for the particular user 101.

In some implementations, the training data 170 may be configured to customize the user, object or task perception of the robot 190.

The training data 170 may include hundreds or millions of images. For example, the example training data 170 depicted in FIG. 1C includes a first image 161, a second image 163, a third image 165, a fourth image 167, a fifth image 169 and a sixth image 171. The example depicted in FIG. 1C depicts less images but may include more images that are not depicted. Accordingly, the example depicted in FIG. 1C is intended to be illustrative and not limiting.

The images included in the training data 170 are grouped into two different sets. The first set 171 includes images of normal daytime activities that a user 101 may perform. For example, the images depict a user running 161, bending over 163, standing 165 or sitting 167. The second set 173 includes images of users who may not be able to bear weight on their legs. For example, the images depict a user sleeping 169, 171 or sitting 167. Note that image 167 is included in each set 171, 173 since the activity of sitting 167 may be associated with either class of images. In other words, sitting is an activity that may be a normal daytime activity or an activity associated with a user who cannot bear weight on their legs.

The motion estimator application 199 may train a user-specific visual classifier using one or more sets of images 171, 173. The motion estimator application 199 may select the images to be used in training the user-specific visual classifier based on the EHR data 111 associated with the user 101 that is associated with the user-specific visual classifier. For example, if the EHR data 111 indicates that a patient has a broken leg or is paralyzed below the waist, then the motion estimator application 199 may select images from the second set 173 of images since these images are more likely to be associated with the disabilities and capabilities of this particular user 101.

Sets 171 and 173 are intended to be illustrative and not limiting. In practice, the training data 170 may include one or more sets of images each describing any class of activities for a user 101 or a robot 190. The classes may be customized for a particular condition that may be included in the EHR data 111. For example, the training data 170 may include a particular class of images associated with Parkinson's disease, Alzheimer's disease, heart disease, different cancers, leg injuries, arm injuries, hand injuries, foot injuries or any other condition or disability that may be described for a user 101 in their particular EHR data 111.

In some implementations, the motion estimator application 199 may provide improved performance by increasing the number of images included in the training data 170. The performance of the motion estimator application 199 may also improve when the images included in the training data depict scenes that are more specific to the actual tasks that the robot 190 will be performing. In some implementations, the motion estimator application 199 may be configured so that the training data 170 may be created or updated on the fly to include more images or images that are more specific to the tasks to be performed by the robot 190.

In some implementations, the perception of the robot 190 may be modified based on the user-specific visual classifier trained using the training data 170. For example, the robot 190 include one or more sensors for perceiving its environment. The robot 190 may identify a user 101 in the environment. The robot 190 may retrieve the user-specific visual classifier associated with the identified user 101. The robot 190 may perceive or interpret the actions or inactions of the user 101 based on the user-specific visual classifier associated with the user 101.

Figure 1D:
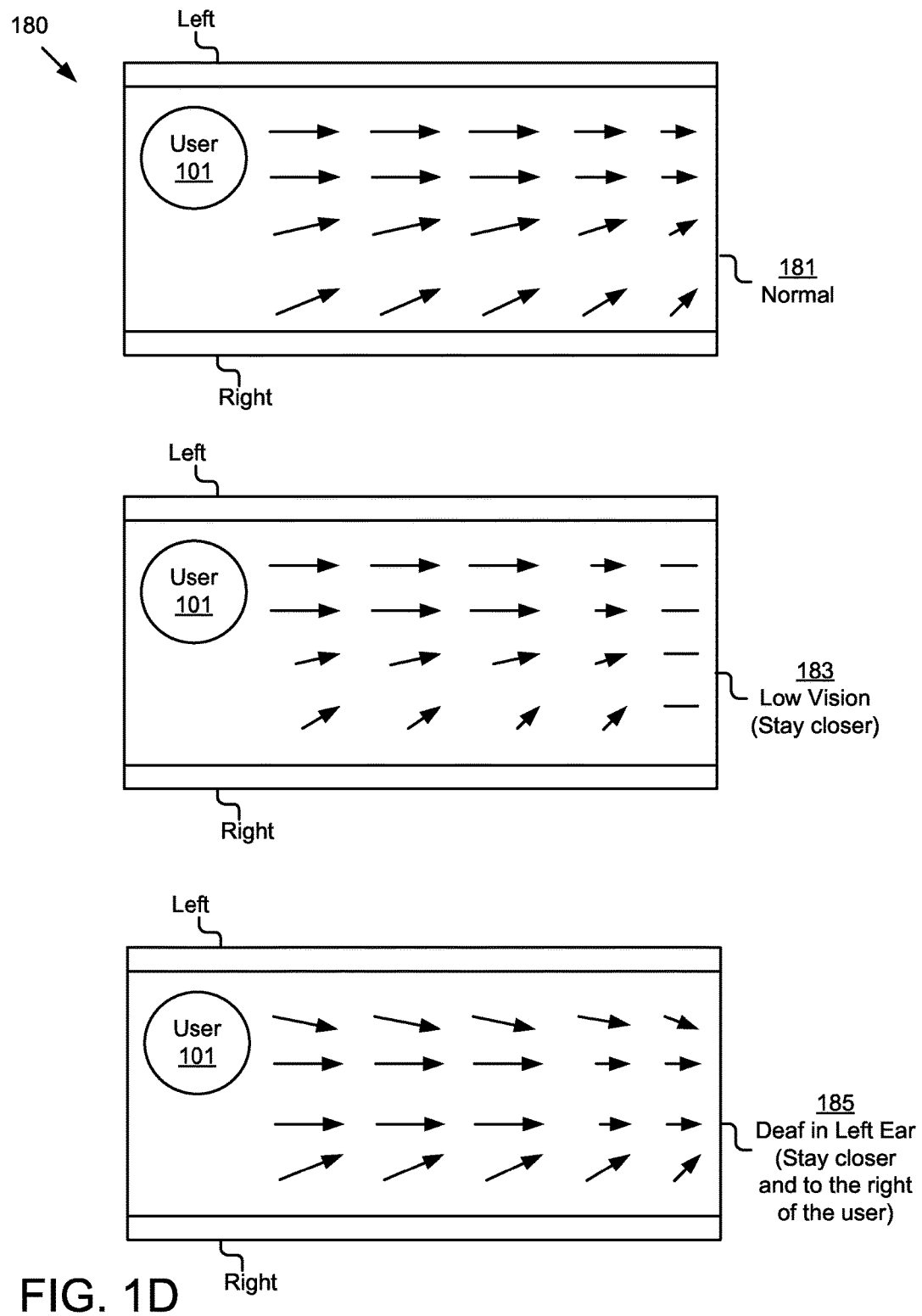
FIG. 1D is a block diagram illustrating examples of the motion estimator application modifying the behavior of a robot when providing navigation assistance.

FIG. 1D is a block diagram illustrating examples 180 of the motion estimator application 199 modifying the behavior of a robot 190 when providing navigation assistance for a user 101. FIG. 1D includes three example scenarios 181, 183, 185 in which a user 101 is being guided down a hallway by a robot 190 (not depicted in FIG. 1D). The arrows indicate the direction the robot 190 should move if it were at any of those positions in he hallway. The longer the arrow, the faster the robot 190 should move.

For normal movement 181, the robot 190 may stay ahead of the user 101 and directly in front of the user 101 so that the robot 190 is visible to the user 101. For example, the robot may maintain a distance of 1.5 to 3 meters from the user 101 while walking.

In scenario 183, the motion estimator application 199 has determined that the EHR data 111 indicates that the user 101 has low vision capabilities. Accordingly, the motion estimator application 199 determines that the program for the robot 190 may be customized for the user 101 so that the robot 190 may stay closer to the user 101 than in scenario 181. The motion estimator application 199 may customize the program of the robot 190 so that the robot 190 stays closer to the user 101 since doing so will make the robot 190 more visible to the user 101. For example, the robot 190 may maintain a distance of 0.3 to 1.5 meters from the user 101. Because the robot 190 stays closer to the user 101, the motion estimator application 199 may also customize the program for the robot 190 so that the robot 190 moves slower or decelerates faster than in scenario 181. For example, in scenario 181 the speed may be 1.2 meters per second, whereas in scenario 183 the speed may be 1.0 meters per second or less depending on the one or more physical capabilities of the user 101. Similarly, the robot 190 may decelerate 10 to 20% faster in scenario 183 versus scenario 181. The shorter arrows for element 183 indicates that the robot 190 is traveling at a lower speed than in scenarios 181 and 185.

In scenario 185, the motion estimator application 199 has determined that the EHR data 111 indicates that the user 101 is deaf in their left ear. Accordingly, the motion estimator application 199 determines that the program for the robot 190 may be customized for the user 101 so that the robot 190 moves faster (1.2 meters per second) than in scenario 183 (1.0 meters per second). For example, the user 101 can still see the robot 190 even though they are partially deaf, and so, there is no risk in harm to the user 101 by causing the robot 190 to move faster. The motion estimator application 199 may also customize the program of the robot 190 so that the robot 190 stays closer to the user 101 since the user 101 may struggle to hear the robot 190. For example, the robot 190 may maintain a distance of 0.3 to 1.5 meters from the user 101. Moreover, the motion estimator application 199 may further customize the program for the robot 190 so that the robot 190 stays to the right and in range of the user's 101 right ear since the user 101 is likely to favor their right ear based on the EHR data 111 indicating deafness in the left ear.

For each of these scenarios 181, 183, 185, the motion estimator application 199 may build a simulation to estimate the functional distance or location at which the robot 190 may travel relative to the user 101. Building such a simulation may be referred to as "perspective taking" The quality of the perspective taking may be increased based on data included in the EHR data 111.

Example Motion Estimator Application

Figure 2:
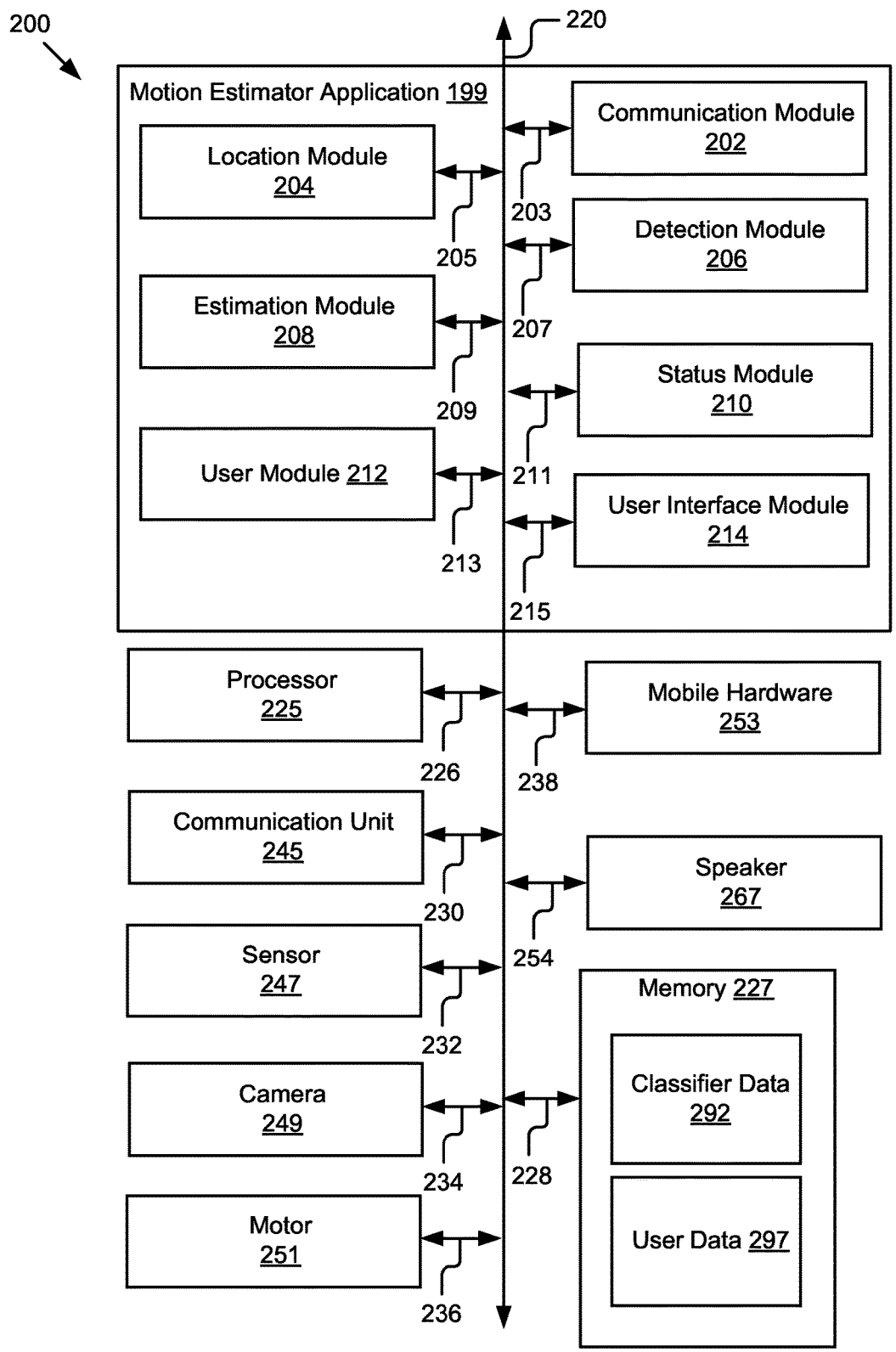
FIG. 2 is a block diagram illustrating an example motion estimator device.

FIG. 2 is a block diagram illustrating an example motion estimator device 200. In some implementations, the motion estimator device 200 may include a special-purpose computing device configured to provide some or all of the functionality described below with reference to FIG. 2.

The motion estimator device 200 can be, or include, or be included in the robot 190 or the computing device 107 in the system 100 illustrated in FIG. 1A. The motion estimator device 200 may include the motion estimator application 199, a processor 225, a memory 227, a communication unit 245, a sensor 247, a camera 249, a motor 251, mobile hardware 253, and a speaker 267 according to some examples. The motion estimator application 199 includes a communication module 202, a location module 204, a detection module 206, an estimation module 208, a status module 210, a user module 212, and a user interface module 214. The components of the motion estimator device 200 are communicatively coupled by a bus 220.

The processor 225 includes an arithmetic logic unit, a microprocessor, a general-purpose controller, or some other processor array to perform computations and provide electronic display signals to a display device. The processor 225 processes data signals and may include various computing architectures including a complex instruction set computer (CISC) architecture, a reduced instruction set computer (RISC) architecture, a graphic processor unit (GPU) architecture or an architecture implementing a combination of instruction sets. Although FIG. 2 includes a single processor 225, multiple processors 225 may be included. Other processors, operating systems, sensors, displays, and physical configurations may be possible. In some implementations, the processor 225 is programmed to perform one or more blocks of the methods 400, 500 described below with reference to FIGS. 4 and 5. The processor 225 is coupled to the bus 220 for communication with the other components via signal line 226.

The memory 227 stores instructions or data that may be executed by the processor 225. The instructions or data may include code for performing the techniques described herein. The memory 227 may include a dynamic random access memory (DRAM) device, a static random access memory (SRAM) device, flash memory, or some other memory device. In some implementations, the memory 227 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis. The memory 227 is coupled to the bus 220 for communication with the other components via signal line 228.

As illustrated in FIG. 2, the memory 227 stores classifier data 292 and user data 297. The memory 227 may also store other data for providing the functionality described herein.

The classifier data 292 may include instructions for the robot 190 for different types of medical conditions. For example, where a medical condition associated with the user 101 is an inability to walk without a wheelchair, the instructions for the robot 190 may include identifying obstacles that may interfere with using the wheelchair and instructions for providing objects to the user 101 by using a hand-over motion that transfers the object to the user 101 to three dimensional point that is proximate to where a hand of the user 101 is at a height that results from sitting in a wheelchair. In some implementations, the motion estimator application 199 observes the user 101 and the robot 190 in simulations to generate classifiers.

The user data 297 may include information about the user 101 including a user identifier (ID), a username and password for the user 101, and/or an EHR for the user 101 that may be retrieved from the health server 110 or generated by the motion estimator application 199. The EHR includes medical conditions associated with the user 101. The motion estimator application 199 may compare medical conditions associated with the user 101 to classifiers that are part of the classifier data 292 to identify instructions for the robot 190 to perform a task.

The communication unit 245 transmits and receives data to and from at least one of the computing device 107, the robot 190, and the health server 110 in the system 100. The communication unit 245 is coupled to the bus 220 via a signal line 230. In some implementations, the communication unit 245 includes a port for direct physical connection to the network 105 or to another communication channel. For example, the communication unit 245 includes a USB, SD, CAT-5, or similar port for wired communication with other entities in the system 100. In some implementations, the communication unit 245 includes a wireless transceiver for exchanging data with other entities in the system 100 or other communication channels using one or more wireless communication methods, including IEEE 802.11, IEEE 802.16, Bluetooth®, or another suitable wireless communication method.

In some implementations, the communication unit 245 includes a cellular communications transceiver for sending and receiving data over a cellular communications network including via short messaging service (SMS), multimedia messaging service (MMS), hypertext transfer protocol (HTTP), direct data connection, WAP, e-mail, or another suitable type of electronic communication. The communication unit 245 may also provide other conventional connections to the network 105 for distribution of files or media objects using standard network protocols including TCP/IP, HTTP, HTTPS, and SMTP, etc.

The sensor 247 is any device that senses physical changes. The sensor 247 is coupled to the bus 220 via signal line 232. In one embodiment, the sensor 247 is a motion detector. For example, the sensor 247 is a gyroscope that measures an orientation of the robot 190. In another example, the sensor 247 is an accelerometer that is used to measure acceleration of the robot 190. In yet another example, the sensor 247 determines location information, for example, by receiving GPS coordinates from a GPS satellite, wireless information, etc. In some implementations, the sensor 247 transmits the location information to the location module 204 via the communication module 202. In other implementations, the sensor 247 stores the location information as part of the classifier data 292 in the memory 227.

The sensor 247 may include a depth sensor. In some implementations, the depth sensor determines depth using structured light, such as a speckle pattern of infrared laser light. In some implementations, the depth sensor determines depth using time-of-flight technology that determines depth based on the time it takes a light signal to travel between the camera and an object. For example, the depth sensor is a laser rangefinder. The depth sensor may be used to identify changes on the ground and the dimensions of the changes including their depth. In some implementations, the sensor 247 transmits the depth information to the location module 204 for identifying the position of the user 101 and obstacles.

In one embodiment, the sensor 247 includes a microphone for detecting sound and converting the sound into electrical signals. The microphone may receive instructions from a visually-impaired user 101 for fulfilling a request. For example, the microphone may receive instructions to pick up an object for a disabled user 101. The microphone transmits the electrical signals to the motion estimator application 199, for example, the status module 210 for processing of the instructions including identifying the change in status.

The camera 249 is a device for capturing images that is coupled to the bus 220 via signal line 234. In one embodiment, the camera 249 captures electronic images. The camera 249 includes an image sensor, such as a charge-coupled device (CCD) or a complementary metal-oxide semiconductor (CMOS) for converting an optical image to electrical signals. In one embodiment, the camera 249 sends the electrical signals to the location module 204 for identifying the position of the user 101, the detection module 206 for detecting the location of obstacles in the environment, and the status module 210 for determining whether the user 101 had a change in status. In some implementations, the camera 249 stores the electrical signals in the memory 227 as part of the classifier data 292 or the user data 297.

In implementations where the motion estimator device 200 is part of a robot 190, the motion estimator device 200 includes a motor 251 and mobile hardware 253. The motor 251 is coupled to the bus 220 via signal line 236. The mobile hardware 253 is coupled to the bus 220 via signal line 238. The motor 251 includes hardware for powering the mobile hardware 253. The mobile hardware 253 includes hardware for moving the robot 190, such as wheels. The motor 251 and the mobile hardware 253 are used to move the robot 190. For example, the estimation module 208 instructs the motor 251 to drive the mobile hardware 253 to perform a task based on obstacles within the environment and one or more physical capabilities of the user 101.

The speaker 267 is optional hardware for generating audible directions that is coupled to the bus 220 via signal line 254. For example, where the motion estimator device 200 is a robot 190, the speaker 267 receives instructions from the estimation module 208 to provide audio directions to a visually-impaired user 101.

In some implementations, each of the modules 202, 204, 206, 208, 210, 212, and 214 in the motion estimator application 199 can include a set of instructions executable by the processor 225 to provide the functionality described below. In some other implementations, each of the modules 202, 204, 206, 208, 210, 212, and 214 can be stored in the memory 227 and can be accessible and executable by the processor 225 of the system. Each of the modules 202, 204, 206, 208, 210, 212, and 214 may be adapted for cooperation and communication with the processor 225 and other components of the motion estimator device 200. In some implementations, each of the modules 202, 204, 206, 208, 210, 212, and 214 may be adapted to function as one or more thin clients that are stored and executed by a processor of the motion estimator device 200.

The communication module 202 can include software including routines for handling communications between the motion estimator application 199 and other components of the motion estimator device 200. In some implementations, the communication module 202 can include a set of instructions executable by the processor 225 to provide the functionality described below for handling communications. The communication module 202 may be communicatively coupled to the bus 220 via signal line 203.

The communication module 202 sends and receives data, via the communication unit 245, to and from one or more of the computing device 107, the robot 190, and the health server 110. For example, the communication module 202 receives, via the communication unit 245, electronic health record data 111 from the health server 110.

In some implementations, the communication module 202 receives data from components of the motion estimator application 199 and stores the data in the memory 227. In some implementations, the communication module 202 retrieves data from the memory 227 and sends the data to one or more components of the motion estimator application 199. For example, the communication module 202 may store images from the camera 249 as user data 297. In some implementations, the communication module 202 may handle communications between components of the motion estimator application 199. For example, the communication module 202 receives data about a location of the user 101 from the location module 204 and sends the data to the estimation module 208.

The location module 204 can include software including routines for determining a current position of a robot 190 and receiving sensor readings on positions, directions, and velocities of the user 101. In some implementations, the location module 204 can include a set of instructions executable by the processor 225 to provide the functionality described below for determining the positions of the robot 190 and the user 101. The location module 204 may be communicatively coupled to the bus 220 via signal line 205.

In some implementations, the location module 204 receives location information from the sensor 247 about the location of the robot 190. For example, the location module 204 receives GPS coordinates from the sensor 247. In another example, the location module 204 receives known locations (e.g., cell towers, WiFi hotspots, etc.) and signal strengths. The location module 204 may determine a current location of the robot 190. For example, the location module 204 determines the location of the robot 190 based on the GPS coordinates, triangulating signals using WiFi, etc. In another example, the location module 204 determines the current location of the robot 190 by receiving images from the camera 249 and comparing the location of known objects in the images to the robot 190.

In some implementations, the location module 204 determines the location of the user 101 based on a medical condition associated with the user 101. For example, the location module 204 receives images from the camera 249 via the communication module 202 based on where the user 101 is expected to be according to the medical condition. For example, where the user 101 cannot bear weight on one or more legs, the user 101 may be more likely to be found sitting, reclining, and/or lying down. As a result, the location module 204 may use a classifier that corresponds to the user 101 that cannot bear weight on one or more legs. The classifier may include instructions for looking for the user 101 at a lower height than if the user 101 could bear weight on both legs.

In some implementations, the location module 204 identifies the location and orientation of the user 101 from images received from the camera 249. The location may be expressed as longitude and latitude coordinates, according to a Cartesian coordinate system. The location module 204 may determine an orientation of the user 101 by identifying a direction of the torso of the user and, based on the direction of the torso of the user 101, the location module 204 may determine a direction of the face of the user 101. The combination of the direction of the torso and the direction of the face may constitute an orientation.

The detection module 206 can include software including routines for detecting obstacles within an environment. In some implementations, the detection module 206 can include a set of instructions executable by the processor 225 to provide the functionality described below for detecting obstacles within an environment. The detection module 206 may be communicatively coupled to the bus 220 via signal line 207.

In some implementations, the detection module 206 identifies objects within an environment. For example, the detection module 206 receives images from the camera 249 and identifies obstacles within the environment. The obstacles may include stationary objects, for example, tables, chairs, doorways, and other things that may obstruct a path of the user 101. The obstacles may also include moving objects, for example, cars, skateboards, bicycles, people, and animals. The detection module 206 may generate a map that includes locations for the obstacles.

In some implementations, the detection module 206 identifies obstacles based on the EHR associated with the user 101. For example, if the user 101 is confined to a wheelchair, some narrow doorways may be impassable by the user 101. In another example, if the user 101 is blind, objects sticking out above the ground may be dangerous to the user 101 because the user 101 might not be able to detect the objects with a walking stick.

The estimation module 208 can include software including routines for estimating one or more physical capabilities of the user 101 based on an EHR associated with the user 101 and generating instructions for a robot 190 to perform a task based on the obstacles within the environment and the one or more physical capabilities of the user 101. In some implementations, the estimation module 208 can include a set of instructions executable by the processor 225 to provide the functionality described below for estimating the one or more physical capabilities of the user 101 and generating instructions for the robot 190 to perform the task. The estimation module 208 may be communicatively coupled to the bus 220 via signal line 209.

The estimation module 208 receives the EHR from the user module 212 via the communication module 202 or from the health server 110 via the communication module 202. The estimation module 208 may identify, from the EHR, medical conditions associated with the user 101 and estimate the one or more physical capabilities of the user 101 based on the medical conditions.

In some implementations, the estimation module 208 may estimate the one or more physical capabilities of the user 101 based on a current medical condition of the user 101. For example, if the user 101 recently had surgery on a right knee, the estimation module 208 determines that the user 101 has limited ability to move their right knee. In some implementations, the estimation module 208 may estimate the one or more physical capabilities of the user 101 based on a historical medical condition of the user 101. For example, the estimation module 208 may determine, based on observations made over a period of time, that the user 101 has limited ability to move on their right side because of an injury in a right shoulder of the user 101. The estimation module 208 may instruct the user module 212 to update the EHR based on the current medical condition or the historical medical condition of the user 101.

In some implementations, the estimation module 208 generates a cost equation based on an EHR associated with the user 101, a current medical condition of the user 101, and/or a historical medical condition of the user 101. The estimation module 208 may apply weights to the cost equation based on observations associated with the user 101. The variables for the estimation module 208 may include a range of motion for the user 101, a reachability for the user 101, muscle tension for the user 101, comfort associated with the user 101, a preference associated with the user 101, a time for the user 101 to pick up the object from the robot 190, a time for the user 101 to make contact with the robot 190 after the robot 190 performs a hand-over motion, and a time of completion of a task.

The estimation module 208 may estimate the one or more physical capabilities of the user 101 based on classifiers for each corresponding medical condition. In some implementations, the estimation module 208 generates classifiers by observing instances of user 101 activity or inactivity in a control with no known medical conditions (or at least not a medical condition that could affect the training) and comparing the control to the user 101 with a known medical condition. The estimation module 208 may collect training data for an extended period of time. For example, the estimation module 208 may observe the control and the user 101 with a medical condition for 24 hours (or 12 hours, 48 hours, etc.).

For example, the estimation module 208 may create a set of classifiers for the user 101 where the user has non-weight bearing legs. The estimation module 208 compares a control with no known medical condition (or no medical condition affecting the legs of the user 101) to the user 101 with non-weight bearing legs. The control user 101 may perform a variety of activities including standing, walking, picking up objects, working at a computer desk, etc. The user 101 with non-weight bearing legs may spend most of the time sitting, reclining, and lying down. The estimation module 208 may generate the classifiers based on the differences between the control and the user 101 and store the classifiers as part of the classifier data 292 in the memory 227.

In some implementations, the estimation module 208 retrieves classifiers from the classifier data 292 stored in the memory 227. The classifiers may be generated offline, independent of the user 101, or created in response to observing the activity or inactivity of the user 101. In some implementations, the estimation module 208 receives images from cameras that are not part of the robot 190 so that a more three-dimensional view of the user 101 may be obtained.

The estimation module 208 may generate classifiers for the user 101 after observing the user 101. The estimation module 208 may estimate the one or more physical capabilities of the user 101 based on a personalized classifier, classifiers associated with a medical condition that the user 101 has, or a combination of both types of classifiers.

The estimation module 208 generates instructions for a robot 190 to perform a task based on obstacles within the environment and the one or more physical capabilities of the user 101. The estimation module 208 may generate a simulation of how the user 101 moves based on the mobility of the user 101 and how the robot 190 should move to accomplish the task based on the obstacles within the environment and the one or more physical capabilities of the user 101. For example, where the user 101 is deaf in a left ear, the estimation module 208 may instruct the robot 190 to travel closer to the user 101 and to the right of the user 101 as compared to how the robot 190 would move in relation to the user 101 without medical conditions. The simulation may use the classifier that corresponds to the medical condition associated with the user 101 to generate the simulation. In some implementations, the estimation module 208 modifies the simulation based on machine learning, system identification, adaptive control, or similar adaption methods.

Alternatively or additionally, the estimation module 208 generates the simulation based on input parameters and a success rate for performing the task successfully. The input parameters may include a speed of the user 101, a relative position of the robot 190 to the user 101, a difficulty of the task, and an amount of information that the robot 190 relays to the user 101 for guidance. The estimation module 208 may simulate how the input parameters affect the success rate.

The estimation module 208 instructs the robot 190 to perform the task. The instructions may be based on the simulation. The task may include retrieving an object for the user 101, providing an object to the user 101, picking up an object from the user 101, providing navigation assistance for the user 101, and carrying an object for the user 101. The estimation module 208 may select, adapt, and/or create behaviors to maximize the success rate for the task.

In some implementations, the estimation module 208 retrieves an object for the user by receiving a request for the object from the user 101, searching an environment for the object, identifying the object in the environment, identifying the user 101 that made the request, and retrieving the identified object for the user 101. The estimation module 208 may receive the request from the user 101 in response to the sensor 247 including a microphone that detects verbal instructions. The estimation module 208 may identify the object in the environment based on the EHR. For example, where the user 101 is confined to a wheelchair, the estimation module 208 determines the sections of the environment that are accessible by the user 101 while the user is in the wheelchair. The estimation module 208 may determine the user 101 that made the request based on, for example, information from the location module 204 and a direction where the verbal instructions were received. As a result of using the above steps to perform object retrieval, the time for searching the environment and object retrieval is advantageously reduced, which makes the robot 190 more useful for the user 101.

Providing the object to the user 101 may include a hand-over motion for moving an object from an original location to a position and rotation in space of a user environment. This may be helpful when the user is wheelchair bound or otherwise finds it difficult to bend down and retrieve objects. In another example, the estimation module 208 determines, based on the medical condition of the user 101 being sciatica, that the user 101 experiences pain if the user 101 carries objects heavier than 20 pounds (or 10 pounds, 30 pounds, etc.). The estimation module 208 may instruct the robot 190 to retrieve a suitcase from a hand of the user 101 and carry it for the user 101 because the suitcase is heavier than 20 pounds.

In some implementations, the estimation module 208 may perform a hand-over motion by determining whether a closest hand that is closest to the robot 190 is injured based on at least one of a range of motion for the closest hand and a reachability for the closest hand. If the closest hand is injured, the estimation module 208 may generate instructions for the robot 190 to perform the hand-over motion for moving an object from an original location to a furthest hand that is furthest from the robot.

The estimation module 208 may provide navigation assistance to the user 101. This may be particularly helpful if the user 101 is a visually-impaired user 101. In some implementations, the estimation module 208 generates a path for the robot 190 to follow and guides the user 101 along the path. The estimation module 208 generates the path based on the one or more physical capabilities of the visually-impaired user 101 by determining whether the visually-impaired user 101 would encounter the obstacles in the environment while travelling along the path. For example, if the visually-impaired user 101 is also wheelchair bound and travelling in a restaurant, the robot 190 may select a path in the restaurant where the distance between tables and chairs is wide enough for the wheelchair used by the visually-impaired user 101 to pass.

The estimation module 208 may determine a beginning and an endpoint of a path based on user input from the user 101. For example, the user 101 may verbally request that the robot 190 provide directions to get to a destination that is received by a sensor 247 functioning as a microphone. The estimation module 208 may perform speech-to-text translation of the request to create machine-understandable language and generate directions accordingly. The beginning of the path may be based on the orientation of the user 101. For example, if the user 101 is facing away from the direction the user 101 should travel to reach the endpoint, the estimation module 208 may generate a path that guides the user 101 to travel in the correct direction.

In some implementations, the estimation module 208 determines the beginning and endpoint of the path based on historical behavior of the user 101. For example, if the visually-impaired user 101 takes the same path Monday through Friday at 8 a.m., if the user 101 requests a path at 8 a.m. on a weekday, the estimation module 208 generates a similar path with the same endpoint that varies based on avoiding obstacles within the environment.

The estimation module 208 may guide the user 101 along the path by generating noises that are broadcast using the speaker 267. Alternatively or additionally, the robot 190 may transmit instructions to a haptic feedback device that is in physical contact with the user 101 that guides the user 101 to move in different directions to follow the path.

The status module 210 can include software including routines for tracking a status associated with the user 101. In some implementations, the status module 210 can include a set of instructions executable by the processor 225 to provide the functionality described below for tracking the status of the user 101. The status module 210 may be communicatively coupled to the bus 220 via signal line 211.

In some implementations, the status module 210 tracks a status associated with the user 101 by determining whether any of the inputs for the simulation generated by the estimation module 208 have changed. For example, where the task is guiding the user 101 and a speed of the user 101 changes, the status module 210 may instruct the estimation module 208, via the communication module 202, to adjust the simulation by updating the speed of the user 101. Alternatively or additionally, the status module 210 may detect feedback from the user 101. For example, the user 101 may provide verbal feedback or provide feedback through a user interface generated by the user interface module 214. The feedback may include asking the robot 190 for help if the robot 190 does not automatically help, telling the robot 190 that the object that the robot 190 retrieved was the wrong object, instructing the robot 190 to put down an object in a particular place if the robot 190 moves past the place, etc.

In some implementations, the status module 210 updates the EHR based on the feedback. The feedback may be based on a misunderstanding of the medical condition of the user 101. For example, if the user 101 previously had a foot injury that was fixed, the user 101 may provide feedback that the foot injury is no longer present. The status module 210 may instruct the user module 212 to update the EHR. The user 101 may provide verbal feedback or feedback through a user interface generated by the user interface module 214.

The user module 212 can include software including routines for generating user data 297. In some implementations, the user module 212 can include a set of instructions executable by the processor 225 to provide the functionality described below for generating the user data 297. The user module 212 may be communicatively coupled to the bus 220 via signal line 213.

In some implementations, the user module 212 registers the user 101. The user module 212 may transmit instructions to the user interface module 214 to display a user interface for receiving information from the user 101. For example, the user interface may include fields for the user 101 to provide a username, demographic information, a medical history including medical conditions associated with the user 101, user preferences associated with the user 101, etc. The user preferences may include, for example, a preference for the robot 190 to retrieve objects for the user 101 that weigh over a certain amount. The user module 212 may receive user input from the user interface module 214 via the communication module 202 and generate an EHR that is particular to the user 101. The user module 212 may store the EHR as part of the user data 297.

Alternatively or additionally, the user module 212 may receive information from data sources outside of the motion estimator device 200. For example, the user module 212 may generate a medical history query and transmit the medical history query to the health server 110 via the communication module 202 to retrieve electronic health record data 111. The user module 212 may identify an EHR for the user 101 from the electronic health record data 111. The user module 212 may receive an encrypted EHR that complies with HIPAA. For example, the user module 212 may use HL7 messaging to receive the EHR. The user module 212 may decrypt the EHR and store the decrypted EHR as user data 297.

The user interface module 214 can include code and routines for generating graphical data for providing user interfaces. In some implementations, the user interface module 214 can include a set of instructions executable by the processor 225 to provide the functionality described below for generating graphical data for providing user interfaces. In some implementations, the user interface module 214 can be stored in the memory 227 of the motion estimator device 200 and can be accessible and executable by the processor 225. The user interface module 214 is coupled to the bus 220 via signal line 215.

In some implementations, the user interface module 214 receives instructions from the user module 212 to generate a user interface for the user 101 to enter user information for registering the user 101. For example, the user interface may include a field for providing a username, a field for providing a password, and one or more fields for providing a medical history, etc. The user interface may include an option for linking the user interface with an EHR from a health server 110.

In some implementations, the user interface module 214 receives instructions from the status module 210 to generate a user interface for the user 101 to provide feedback. The feedback may include an option to update the medical history with medical information. For example, the user 101 may add a newly diagnosed medical condition or remove a current medical condition that was fixed.

Figure 3:
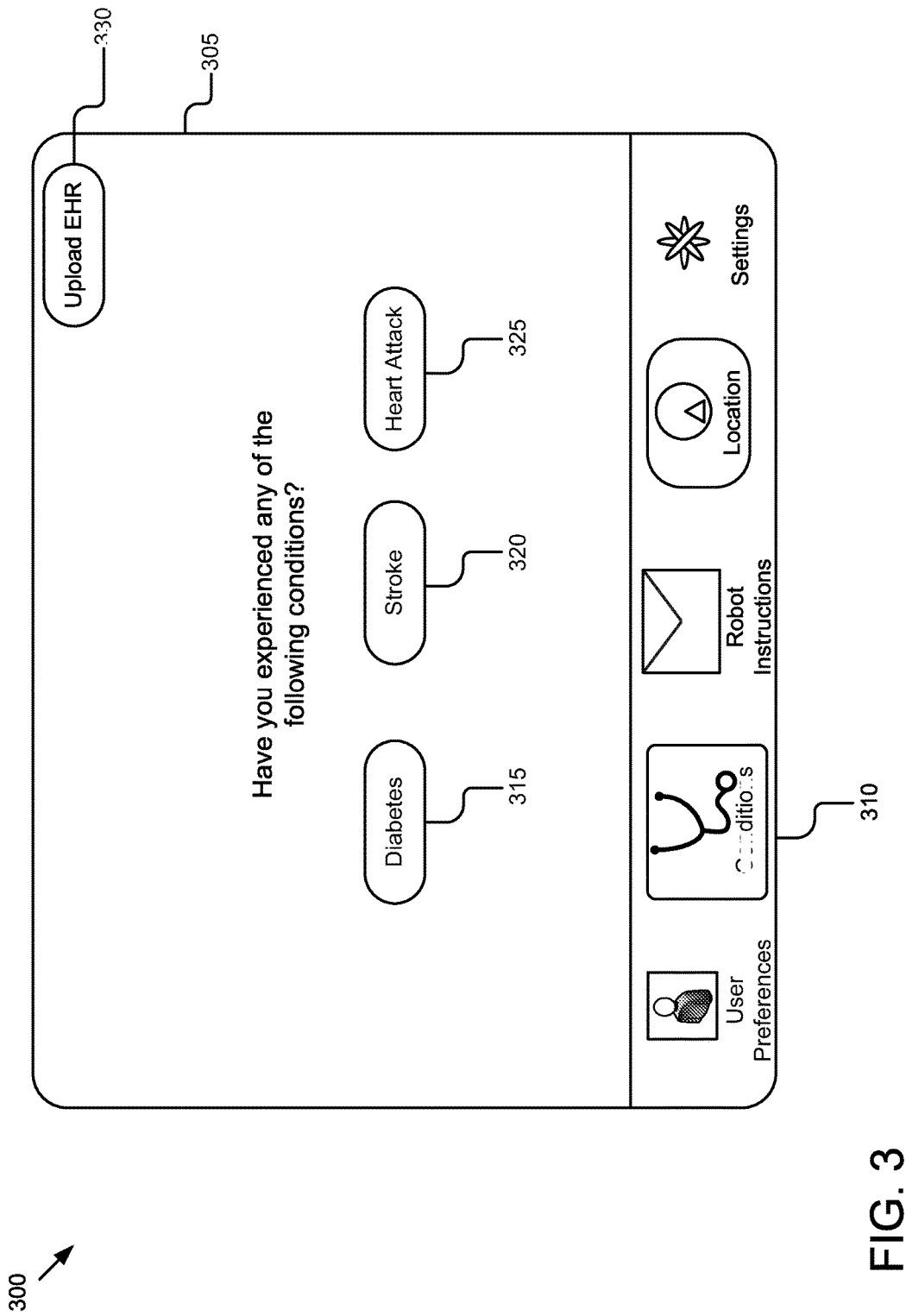
FIG. 3 is a graphic illustrating a user interface that accepts user input for providing a medical history.

Turning now to FIG. 3, an example user interface is illustrated. FIG. 3 is a graphic illustrating a user interface 300 that accepts user input for providing a medical history. The user interface 300 is divided into a top panel 305 and a bottom panel 310 that are generated by the user interface module 214. The top panel 305 includes the question: "Have you experienced any of the following conditions?" In this example, the answers to the question include buttons for selecting a Diabetes icon 315, a Stroke icon 320, and a Heart Attack icon 325. Selecting any of the answers may cause the user interface module 214 to generate a user interface with additional questions about the answer. For example, selecting the Heart Attack icon 325 may cause the user interface module 214 to generate a user interface that asks the user 101 about the number of heart attacks experienced by the user 101, the dates of the heart attacks, whether the user 101 is taking medication to treat conditions associated with the heart attacks, etc. The user module 212 may generate an EHR based on the answers.

The top panel 305 also includes an Upload EHR icon 330 that, when selected, causes the user interface module 214 to generate a user interface for linking the user interface with an EHR for the user 101. This may be advantageous because it would reduce the time it would take the user 101 to input the medical history and it may include a more accurate medical history based on a doctor's notes instead of the imprecise information provided by the user.

The bottom panel 310 includes other icons that, when selected, cause the user interface module 214 to generate a user interface for the corresponding icon. The icons include user preferences, conditions, robot instructions, a location, and settings.

Example Methods

Figure 4:
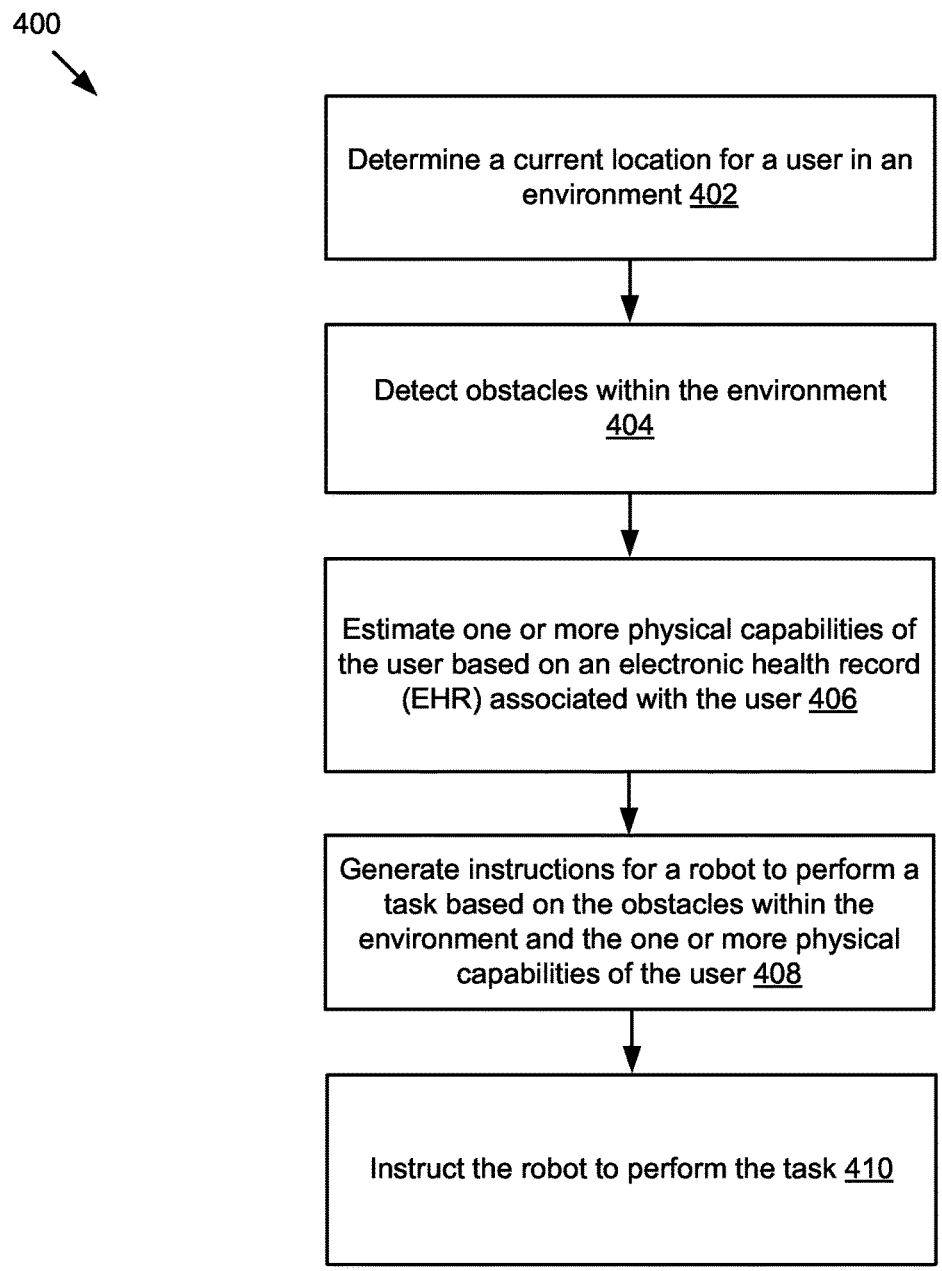
FIG. 4 is a flowchart of an example method for providing personalized patient care based on an electronic health record associated with a user.

Referring now to FIG. 4, a flowchart of an example method 400 for determining a robot task based on user one or more physical capabilities is described. In some implementations, one or more blocks of the method 400 may be performed by a processor-based computing device programmed to perform the one or more blocks of the method 400. For example, one or more steps of the method 400 may be performed by a mobile computing device programmed to perform the one or more steps of the method 400. Alternatively or additionally, the method 400 may be performed by modules of the motion estimator application 199 stored on the computing device 107 or the robot 190 in FIG. 1A. For example, the motion estimator application 199 may include the location module 204, the detection module 206, and the estimation module 208 of FIG. 2.

At block 402, a current location for a user in an environment is determined. For example, the location module 204 determines the current location for the user 101 in the environment. The location may be determined based on information provided by the sensor 247. For example, the location module 204 may determine the location of the robot 190 from GPS coordinates provided by the sensor 247. The location module 204 may then use images received from the camera 249 to determine the position of the user 101 in relation to the robot 190. Alternatively or additionally, the location module 204 may receive sensor readings on positions, directions, and velocities of the user 101.

At block 404, obstacles within the environment may be detected. For example, the detection module 206 may detect obstacles within the environment including stationary objects (e.g., tables and chairs) and moving objects (e.g., people and bicycles).

At block 406, a one or more physical capabilities of the user may be estimated based on an EHR associated with the user. The estimation module 208 may estimate the one or more physical capabilities of the user 101 based on an EHR associated with the user 101. For example, the estimation module 208 may estimate that the user 101 has limited physical capabilities based on poor vision.

At block 408, instructions are generated for a robot to perform a task based on the obstacles within the environment and the one or more physical capabilities of the user. The estimation module 208 may instruct the robot 190 to perform the task based on the obstacles within the environment and the one or more physical capabilities of the user 101. For example, the task may be assisting the user 101 in travelling in a facility by providing navigation assistance and carrying luggage for the user 101. The estimation module 208 may determine that the robot 190 should travel closer to the user 101 than if the user 101 had normal vision because the user 101 needs the robot 190 to stay visible. As a result, the estimation module 208 determines that the robot 190 should travel more slowly than as compared to a person with normal vision.

At block 410, the robot is instructed to perform the task. The robot 190 may be instructed to perform the task. For example, the estimation module 208 instructs the robot 190 to perform the task by transmitting instructions to a motor 251, which controls mobile hardware 253 to perform the navigation assistance and carrying of luggage.

Figure 5:
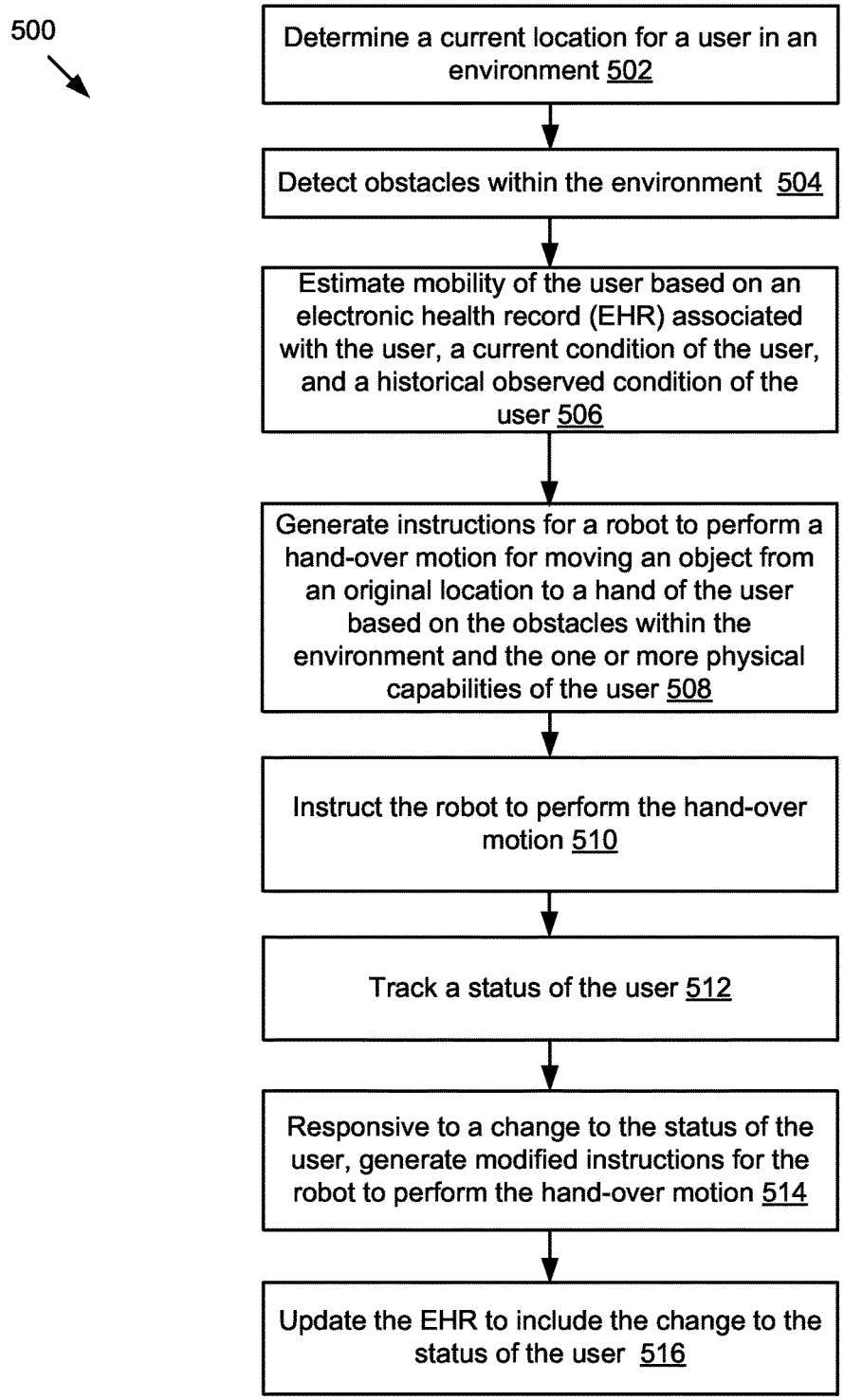
FIG. 5 is a flowchart of an example method for determining a hand-over-motion to be performed by a robot.

FIG. 5 is a flowchart of an example method 500 for determining a hand-over-motion to be performed by a robot. In some implementations, one or more blocks of the method 500 may be performed by a processor-based computing device programmed to perform the one or more blocks of the method 500. For example, one or more steps of the method 500 may be performed by a mobile computing device programmed to perform the one or more steps of the method 500. Alternatively or additionally, the method 500 may be performed by modules of the motion estimator application 199 stored on the computing device 107 or the robot 190 in FIG. 1A. For example, the motion estimator application 199 may include the location module 204, the detection module 206, the estimation module 208, the status module 210, and the user module 212 of FIG. 5.

At block 502, a current location for a user in an environment is determined. For example, the location module 204 determines the current location for the user 101 in the environment. The location module 204 may determine the current location for the user 101 based on information from the sensors 247.

At block 504, obstacles within the environment are determined. For example, the detection module 206 detects obstacles within the environment. The detection module 206 may detect the location of stationary objects and moving objects.

At block 506, the one or more physical capabilities of the user may be estimated based on an EHR associated with the user. The estimation module 208 may estimate the one or more physical capabilities of the user 101 based on an EHR associated with the user 101. For example, the estimation module 208 determines that the user 101 has a medical condition of a weak left elbow based on the EHR. The estimation module 208 may generate a simulation to determine the one or more physical capabilities of the user 101 that includes input parameters about the limitations of the weak left elbow, as well as observational data that the user 101 lies in bed, cannot stand easily, and has an IV on a right hand of the user 101, which causes a level of discomfort. The estimation module 208 determines from the simulation that the user 101 can easily stand and comfortably hold an object if the user 101 holds the object close to the body with a left hand of the user 101.

At block 508, instructions are generated for a robot to perform a hand-over motion for moving an object from an original location to a position and rotation in space of the user environment based on the obstacles within the environment and the one or more physical capabilities of the user. For example, the estimation module 208 may generate instructions for the robot 190 to perform the hand-over motion for moving the object from the original location to the position and rotation in space of the user environment based on the obstacles within the environment and the one or more physical capabilities of the user 101. Continuing with the example above, the estimation module 208 generates instructions for the robot 190 to perform a hand-over motion that targets a left-handed retrieval to avoid the injured right hand of the user 101.

At block 510, the robot is instructed to perform the hand-over motion. The estimation module 208 may instruct the robot 190 to perform the hand-over motion. For example, the estimation module 208 instructs the robot 190 to perform the hand-over motion by transmitting instructions to a motor 251, which controls mobile hardware 253.

At block 512, a status of the user is tracked. For example, the status module 210 tracks the status of the user 101. The status module 210 may track the status by receiving images from the camera 249 and determining whether input parameters for the simulation have changed. For example, if the user 101 changes from a sitting position to a standing position, the status module 210 determines that the status of the user 101 changed.

At block 514, responsive to a change in the status of the user, modified instructions are generated for the robot to perform the hand-over motion. For example, responsive to the change in the status of the user, the status module 210 may generate modified instructions for the robot 190 to perform the hand-over motion. The status module 210 may instruct the robot 190 to perform the hand-over motion by giving the object to the user 101 who is now standing instead of sitting.

At block 516, the EHR is updated to include the change to the status of the user. The user module 212 may update the EHR to include the change to the status of the user. For example, the user module 212 may update the EHR to reflect that the user 101 is capable of standing.

Figure 6:
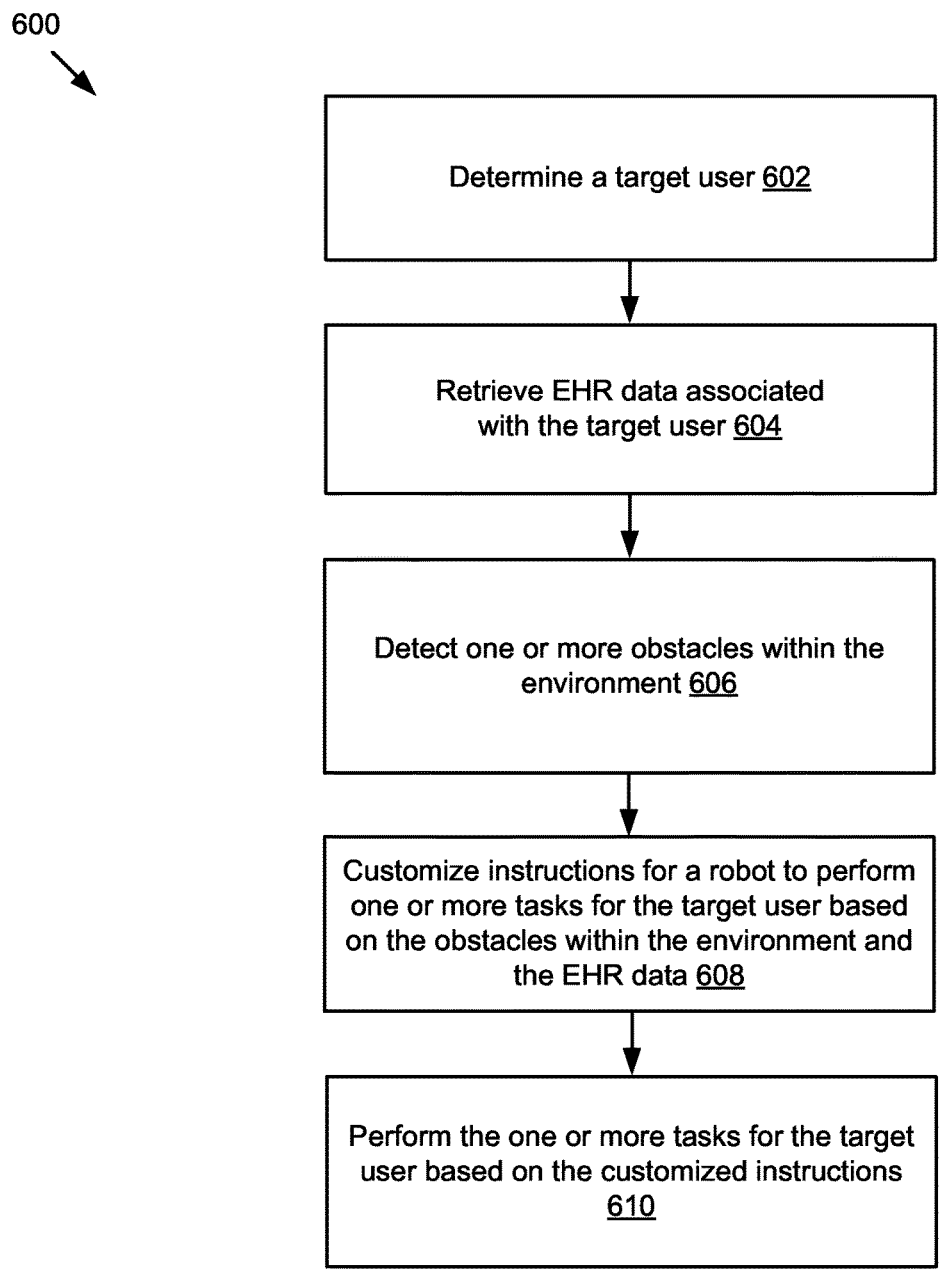
FIG. 6 is a flowchart of an example method for performing a task that includes finding and recognizing a target user.

Referring now to FIG. 6, a flowchart of an example method 600 for performing a task that includes finding and recognizing a target user is described. In some implementations, one or more blocks of the method 600 may be performed by a processor-based computing device programmed to perform the one or more blocks of the method 600. For example, one or more steps of the method 600 may be performed by a mobile computing device programmed to perform the one or more steps of the method 600. Alternatively or additionally, the method 600 may be performed by modules of the motion estimator application 199 stored on the computing device 107 or the robot 190 in FIG. 1A. For example, the motion estimator application 199 may include the location module 204, the detection module 206, and the estimation module 208 of FIG. 2.

At block 602, a target user is determined. For example, the location module 204 determines that the user 101 is the target user. In some implementations, a medical professional such as a doctor or nurse may define the target user for the robot 190. For example, a nurse may instruct the robot 190 to provide a glass of water to a patient who is the target user for the robot 190.

At block 604, the EHR data 111 for the target user may be retrieved. For example, the motion estimator application 199 may determine a query for retrieving the EHR data 111 associated with the target user from a database stored on the health server 110 or the robot 190. The EHR data 111 may describe one or more physical capabilities of the target user.

At block 606, obstacles within the environment may be detected. For example, the detection module 206 may detect obstacles within the environment including stationary objects (e.g., tables and chairs) and moving objects (e.g., people and bicycles).

At block 608, customized instructions may be generated for the robot 190 to perform one or more tasks for the target user based on the obstacles within the environment and the EHR data 111. In this way, the instructions for performing the task may be customized based on the obstacles in the environment and the one or more physical capabilities of the user as described by the EHR data 111. In some implementations, the task may include finding and recognizing the target user in the environment. The task may further include handing an object to the target user. For example, the robot 190 may hand a glass of water to the target user.

At block 610, the robot 190 may perform one or more tasks for the target user based on the customized instructions. For example, the robot 190 may find and recognize the target user, and then provide the target user with a glass of water as instructed by the nurse.

In the above description, for purposes of explanation, numerous specific details are set forth in order to provide a thorough understanding of the specification. It will be apparent, however, to one skilled in the art that the disclosure can be practiced without these specific details. In some instances, structures and devices are shown in block diagram form in order to avoid obscuring the description. For example, the implementations can be described above primarily with reference to user interfaces and particular hardware. However, the implementations can apply to any type of computing device that can receive data and commands, and any peripheral devices providing services.

Reference in the specification to "some implementations" or "some instances" means that a particular feature, structure, or characteristic described in connection with the implementations or instances can be included in at least one implementation of the description. The appearances of the phrase "in some implementations" in various places in the specification are not necessarily all referring to the same implementations.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The implementations of the specification can also relate to a processor for performing one or more steps of the methods described above. The processor may be a special-purpose processor selectively activated or reconfigured by a computer program stored in the computer. Such a computer program may be stored in a computer-readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory, or any type of media suitable for storing electronic instructions, each coupled to a computer system bus.

The specification can take the form of some entirely hardware implementations, some entirely software implementations or some implementations containing both hardware and software elements. In some preferred implementations, the specification is implemented in software, which includes, but is not limited to, firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A data processing system suitable for storing or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including, but not limited to, keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem, and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the implementations of the specification has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions, or formats. Furthermore, as will be apparent to one of ordinary skill in the relevant art, the modules, routines, features, attributes, methodologies, and other aspects of the disclosure can be implemented as software, hardware, firmware, or any combination of the three. Also, wherever a component, an example of which is a module, of the specification is implemented as software, the component can be implemented as a standalone program, as part of a larger program, as a plurality of separate programs, as a statically or dynamically linked library, as a kernel-loadable module, as a device driver, or in every and any other way known now or in the future to those of ordinary skill in the art of computer programming. Additionally, the disclosure is in no way limited to implementation in any specific programming language, or for any specific operating system or environment. Accordingly, the disclosure is intended to be illustrative, but not limiting, of the scope of the specification, which is set forth in the following claims.

What is claimed is:

1. A method comprising:
   determining a current location for a user in an environment;
   detecting obstacles within the environment;
   estimating one or more physical capabilities of the user based on an electronic health record (EHR) associated with the user, wherein the EHR includes a description of a current medical condition of the user and a historical medical condition of the user and estimating the one or more physical capabilities of the user includes a processor executing a simulation which estimates the one or more physical capabilities of the user based on the current medical condition of the user and the historical medical condition of the user, wherein the simulation indicates a goal for the user which is estimated to improve an experience of the user by increasing one of comfort and ease for the user;

generating instructions for a robot to perform a hand-over motion for moving an object from an original location to a position and a rotation within the environment, wherein the instructions are generated based on the obstacles within the environment, the one or more physical capabilities of the user and the goal indicated by the simulation, wherein the goal includes one or more of the position and the rotation of the hand-over motion which are each estimated by the simulation to improve the experience of the user by increasing one of comfort and ease for the user for the hand-over motion;

instructing the robot to perform the hand-over motion, wherein instructing the robot includes determining, by the processor, whether a closest hand that is closest to the robot is injured based on at least one of a range of motion for the closest hand and a reachability for the closest hand; and, responsive to the closest hand being injured, computing by the processor, the hand-over motion for moving the object from the original location to a furthest hand that is furthest from the robot;

tracking a status of the user;

responsive to a change to the status of the user, generating modified instructions for the robot to perform the hand-over motion; and updating the EHR to include the change to the status of the user.

2. A method comprising:

determining a current location for a user in an environment;

detecting obstacles within the environment;

estimating, by a processor, one or more physical capabilities of the user based on an electronic health record (EHR) associated with the user, wherein estimating the one or more physical capabilities of the user includes the processor executing a simulation to determine the one or more physical capabilities of the user based on the EHR and the simulation indicates a goal for the user which improves an experience of the user;

generating, by the processor, instructions for a robot to perform a task based on the obstacles within the environment, the one or more physical capabilities of the user and the goal indicated by the simulation, wherein the goal includes an outcome of the task which is estimated by the simulation to improve the experience of the user by increasing one of comfort and ease of the user for the task;

instructing the robot to perform the task, wherein the task includes a hand-over motion and instructing the robot includes determining, by the processor, whether a closest hand that is closest to the robot is injured based on at least one of a range of motion for the closest hand and a reachability for the closest hand; and, responsive to the closest hand being injured, computing by the processor, the hand-over motion for moving an object from an original location to a furthest hand that is furthest from the robot;

tracking a status of the user while performing the task; and responsive to a change to the status of the user, generating modified instructions for the robot to perform the task.

3. The method of claim 2, wherein the hand-over motion includes moving the object from the original location to a position and a rotation within the environment and the simulation indicates the position and the rotation which are each described by the goal.

4. The method of claim 2, wherein estimating the one or more physical capabilities of the user is further based on at least one of a current medical condition of the user and a historical medical condition of the user.

5. The method of claim 4, wherein:

the hand-over motion includes moving the object from the original location to a position and a rotation within the environment and the simulation indicates the position and the rotation which are each described by the goal; and the historical medical condition includes at least one of a range of motion for the user, reachability for the user, muscle tension for the user, comfort associated with the user, a preference associated with the user, a time for the user to pick up the object from the robot, a time for the user to make contact with the robot after the hand-over motion, and a time of completion of the task.

6. The method of claim 2, wherein estimating the one or more physical capabilities of the user is further based on user preferences associated with the user.

7. The method of claim 2, wherein the task includes carrying the object for the user.

8. The method of claim 2, wherein the task includes estimating a path for the user to travel, wherein estimating the path for the robot to travel is based on at least one of a speed of the user, a relative position to the user, a difficulty of the path, and an amount of information the robot provides to the user for guidance, and further comprising:

instructing the robot to guide the user by traveling along the path.

9. The method of claim 8, further comprising determining a condition of the user based on the EHR and wherein estimating the path includes estimating a distance between the robot and the user based on the condition of the user.

10. The method of claim 2, wherein estimating the one or more physical capabilities of the user based on the EHR further comprises the processor:

building an EHR query;

querying a database for the EHR;

receiving the EHR; and generating the simulation based on the EHR.

11. The method of claim 10, wherein generating the simulation includes the processor generating classifiers and training sets that are used to identify a condition associated with the user.

12. The method of claim 11, further comprising the processor:

updating the EHR to include a change to the status of the user.

13. The method of claim 2, wherein each step of the method is executed by the robot.

14. A non-transitory computer-readable medium having computer instructions stored thereon that are executable by a processor of a robot to perform or control performance of steps comprising:

determining a current location for a user in an environment;

detecting obstacles within the environment;

estimating one or more physical capabilities of the user based on an electronic health record (EHR) associated with the user, wherein estimating the one or more physical capabilities of the user includes the processor of the robot executing a simulation to determine the one or more physical capabilities of the user based on the EHR, wherein the simulation indicates a goal for the user which improves an experience of the user;

generating instructions for the robot to perform a task based on the obstacles within the environment, the one or more physical capabilities of the user and the goal, wherein the goal includes an outcome of the task which is estimated by the simulation to improve the experience of the user by increasing one of comfort and ease for the user for the task;

instructing the robot to perform the task, wherein the task includes a hand-over motion and instructing the robot includes determining, by the processor, whether a closest hand that is closest to the robot is injured based on at least one of a range of motion for the closest hand and a reachability for the closest hand; and, responsive to the closest hand being injured, computing by the processor, the hand-over motion for moving an object from an original location to a furthest hand that is furthest from the robot;

tracking a status of the user while performing the task; and responsive to a change to the status of the user, generating modified instructions for the robot to perform the task.

15. The non-transitory computer-readable medium of claim 14, wherein:

the hand-over motion includes moving the object from the original location to a position and a rotation within the environment, wherein the position and the rotation are described by the goal which is indicated by the simulation; and estimating the one or more physical capabilities of the user is further based on at least one of a current medical condition of the user and a historical medical condition of the user, the historical medical condition including at least one of a range of motion for the user, reachability for the user, muscle tension for the user, comfort associated with the user, a time for the robot to pick up the object with a hand, a time for the hand-over motion, and a time of completion of the task.

16. The non-transitory computer-readable medium of claim 15, wherein the task includes carrying the object for the user.

17. The non-transitory computer-readable medium of claim 15, wherein the task includes estimating a path for the user to travel, wherein estimating the path for the robot to travel is based on at least one of a speed of the user, a relative position to the user, a difficulty of the path, and an amount of information the robot provides to the user for guidance, and the steps further comprising:

instructing the robot to guide the user by traveling along the path.

18. The non-transitory computer-readable medium of claim 17, the steps further comprising determining a condition of the user based on the EHR and wherein estimating the path includes estimating a distance between the robot and the user based on the condition of the user.

19. The non-transitory computer-readable medium of claim 15, wherein estimating the one or more physical capabilities of the user based on the EHR further comprises:

building an EHR query;

querying a database for the EHR;

receiving the EHR; and generating the simulation based on the EHR.

20. A computer program product stored on a non-transitory memory of a robot that, when executed by a processor, causes the processor to execute steps including:

determining a current location for a user in an environment;

detecting obstacles within the environment;

estimating one or more physical capabilities of the user based on an electronic health record (EHR) associated with the user, wherein the EHR includes a description of a current medical condition of the user and a historical medical condition of the user and estimating the one or more physical capabilities of the user includes the processor executing a simulation which estimates the one or more physical capabilities of the user based on the current medical condition of the user and the historical medical condition of the user, wherein the simulation indicates a goal for the user which is estimated to improve an experience of the user by increasing one of comfort and ease for the user;

generating instructions for the robot to perform a hand-over motion for moving an object from an original location to a position and a rotation within the environment, wherein the instructions are generated based on the obstacles within the environment, the one or more physical capabilities of the user and the goal indicated by the simulation, wherein the goal includes one or more of the position and the rotation of the hand-over motion which are each estimated by the simulation to improve the experience of the user by increasing one of comfort and ease for the user for the hand-over motion;

instructing the robot to perform the hand-over motion, wherein instructing the robot includes determining, by the processor, whether a closest hand that is closest to the robot is injured based on at least one of a range of motion for the closest hand and a reachability for the closest hand; and, responsive to the closest hand being injured, computing by the processor, the hand-over motion for moving the object from the original location to a furthest hand that is furthest from the robot;

tracking a status of the user; and responsive to a change to the status of the user, generating modified instructions for the robot to perform the hand-over motion.

21. The computer program product of claim 20, wherein the hand-over motion is performed based on a preference of the user.

22. The computer program product of claim 20, wherein estimating the one or more physical capabilities of the user is further based on user preferences associated with the user.

23. The computer program product of claim 20, wherein the hand-over motion is performed if the object weighs more than a threshold amount of weight.

24. The computer program product of claim 20, wherein the hand-over motion is not performed if the object does not weigh more than a threshold amount of weight.

* * * * *